(12) United States Patent
Boege et al.

(10) Patent No.: US 7,387,891 B2
(45) Date of Patent: *Jun. 17, 2008

(54) OPTICAL INSTRUMENT INCLUDING EXCITATION SOURCE

(75) Inventors: Steven J. Boege, San Mateo, CA (US); Mark F. Oldham, Los Gatos, CA (US); Eugene F. Young, Marietta, GA (US)

(73) Assignee: Applera Corporation, Foster City, CA (US)

( * ) Notice: Subject to any disclaimer, the term of this patent is extended or adjusted under 35 U.S.C. 154(b) by 623 days.

This patent is subject to a terminal disclaimer.

(21) Appl. No.: 10/440,719

(22) Filed: May 19, 2003

(65) Prior Publication Data
US 2004/0038390 A1 Feb. 26, 2004

Related U.S. Application Data

(63) Continuation-in-part of application No. 10/216,620, filed on Aug. 9, 2002, now Pat. No. 7,008,789, which is a continuation of application No. 09/700,536, filed as application No. PCT/US99/11088 on May 17, 1999, now Pat. No. 6,818,437.

(60) Provisional application No. 60/381,671, filed on May 17, 2002, provisional application No. 60/409,152, filed on Sep. 9, 2002, provisional application No. 60/450,734, filed on Feb. 28, 2003.

(51) Int. Cl.
| | |
|---|---|
| C12M 1/34 | (2006.01) |
| C12M 3/00 | (2006.01) |
| G01N 21/64 | (2006.01) |
| G01N 21/66 | (2006.01) |
| F21V 9/16 | (2006.01) |

(52) U.S. Cl. .............. 435/288.7; 435/288.7; 435/288.4; 435/808; 422/82.08; 378/42; 378/45; 250/483.1; 250/459.1; 250/461.2

(58) Field of Classification Search .............. 435/288.7, 435/288.4, 808; 422/82.08; 378/42, 45; 250/483.1, 459.1, 461.2
See application file for complete search history.

(56) References Cited

U.S. PATENT DOCUMENTS
3,973,129 A * 8/1976 Blumberg et al. ........ 250/461.2

(Continued)

FOREIGN PATENT DOCUMENTS
EP 0 065 409 A2 11/1982

(Continued)

OTHER PUBLICATIONS

H.W. Sands Corp., *OLED Emitters Selected By Color Emission*, http://www.hwsands.com/productlists/oled/oled_emitters_color_emission.htm (Printed Jan. 10, 2003).

(Continued)

*Primary Examiner*—William H. Beisner
*Assistant Examiner*—Nathan Bowers
(74) *Attorney, Agent, or Firm*—Kilyk & Bowersox, P.L.L.C.

(57) ABSTRACT

An optical instrument is provided for simultaneously illuminating two or more spaced-apart reaction regions with an excitation beam generated by a light source. A collimating lens can be disposed along a beam path between the light source and the reaction regions to form bundles of collimated excitation beams, wherein each bundle corresponds to a respective reaction region. Methods of analysis using the optical instrument are also provided.

74 Claims, 13 Drawing Sheets

U.S. PATENT DOCUMENTS

| | | | |
|---|---|---|---|
| 4,284,897 A | 8/1981 | Sawamura et al. ...... 250/461 B |
| 4,626,684 A | 12/1986 | Landa ...................... 250/328 |
| 4,643,877 A | 2/1987 | Opitz et al. .................. 422/68 |
| 4,673,289 A | 6/1987 | Gaucher ..................... 356/72 |
| 4,683,202 A | 7/1987 | Mullins ...................... 435/91 |
| 5,073,029 A | 12/1991 | Eberly et al. ............... 356/432 |
| 5,091,652 A | 2/1992 | Mathies et al. ........... 250/458.1 |
| 5,169,601 A | 12/1992 | Ohta et al. ................... 422/73 |
| 5,215,883 A | 6/1993 | Chu ............................. 435/6 |
| 5,243,540 A | 9/1993 | Van Albert et al. ......... 364/500 |
| 5,256,880 A | 10/1993 | Loree et al. .............. 250/461.1 |
| 5,315,375 A | 5/1994 | Allen ......................... 356/417 |
| 5,355,215 A | 10/1994 | Schroeder et al. .......... 356/317 |
| 5,371,016 A | 12/1994 | Berndt ........................ 435/291 |
| 5,383,023 A | 1/1995 | Walleczek .................. 356/417 |
| 5,389,544 A | 2/1995 | Sugata et al. ............... 435/291 |
| 5,424,841 A * | 6/1995 | Van Gelder et al. ......... 356/417 |
| 5,475,610 A | 12/1995 | Atwood et al. .............. 364/500 |
| 5,547,849 A | 8/1996 | Baer et al. .................. 435/7.24 |
| 5,567,947 A | 10/1996 | Kebabian ................. 250/458.1 |
| 5,595,708 A | 1/1997 | Berndt .................... 422/82.06 |
| 5,656,493 A | 8/1997 | Mullis et al. ............. 435/286.1 |
| 5,672,880 A | 9/1997 | Kain ........................ 250/458.1 |
| 5,736,333 A | 4/1998 | Livak et al. .................... 435/6 |
| 5,759,781 A | 6/1998 | Ward et al. ...................... 435/6 |
| 5,766,889 A | 6/1998 | Atwood ..................... 435/91.2 |
| 5,779,978 A | 7/1998 | Hartmann et al. ........ 422/82.05 |
| 5,792,610 A | 8/1998 | Witney et al. .................. 435/6 |
| 5,846,842 A | 12/1998 | Herron et al. ............... 436/518 |
| 5,854,684 A | 12/1998 | Stabile et al. ............... 356/440 |
| 5,863,502 A | 1/1999 | Southgate et al. ............. 422/58 |
| 5,872,623 A * | 2/1999 | Stabile et al. .................. 356/73 |
| 5,926,271 A | 7/1999 | Couderc et al. ............. 356/318 |
| 5,943,129 A | 8/1999 | Hoyt et al. .................. 356/318 |
| 6,040,940 A | 3/2000 | Kawasaki ................... 359/389 |
| 6,057,114 A | 5/2000 | Akong et al. ............... 435/7.21 |
| 6,066,245 A * | 5/2000 | Trost ........................... 204/461 |
| 6,096,272 A | 8/2000 | Clark et al. ................... 422/64 |
| 6,197,575 B1 | 3/2001 | Griffith et al. ............ 435/288.4 |
| 6,229,635 B1 * | 5/2001 | Wulf ........................... 359/196 |
| 6,287,871 B1 | 9/2001 | Herron et al. ............... 436/172 |
| 6,309,601 B1 | 10/2001 | Juncosa et al. ............. 422/68.1 |
| 6,316,774 B1 * | 11/2001 | Giebeler et al. .......... 250/458.1 |
| 6,331,438 B1 | 12/2001 | Aylott et al. ................ 436/172 |
| 6,337,740 B1 | 1/2002 | Parce ........................... 356/344 |
| 6,352,672 B1 | 3/2002 | Mabile et al. ............ 422/82.08 |
| 6,355,934 B1 * | 3/2002 | Osgood et al. ........... 250/458.1 |
| 6,364,516 B1 | 4/2002 | Li et al. ....................... 362/553 |
| 6,388,788 B1 | 5/2002 | Harris et al. ................ 359/196 |
| 6,411,835 B1 | 6/2002 | Modell et al. ............... 600/407 |
| 6,455,861 B1 * | 9/2002 | Hoyt ....................... 250/458.1 |
| 6,529,275 B2 | 3/2003 | Amirkhanian et al. ...... 356/413 |
| 6,686,582 B1 | 2/2004 | Völcker et al. |
| 6,929,953 B1 * | 8/2005 | Wardlaw ...................... 436/63 |
| 7,202,953 B1 * | 4/2007 | Mueller et al. .............. 356/445 |
| 2001/0033374 A1 | 10/2001 | Hoyt |
| 2002/0060791 A1 | 5/2002 | Stumbo et al. |
| 2002/0109100 A1 * | 8/2002 | Jackson et al. ........... 250/458.1 |
| 2002/0146688 A1 | 10/2002 | Kinjo |
| 2002/0185610 A1 * | 12/2002 | Stern ....................... 250/458.1 |
| 2004/0253714 A1 * | 12/2004 | Trulson et al. ........... 435/287.2 |
| 2005/0057749 A1 * | 3/2005 | Dietz et al. ................. 356/318 |

FOREIGN PATENT DOCUMENTS

| | | |
|---|---|---|
| EP | 0 640 828 A1 | 3/1995 |
| EP | 0 987 539 A1 | 3/2000 |
| JP | 07-120392 | 5/1995 |
| JP | 07-120393 | 5/1995 |
| JP | 07-174701 | 7/1995 |
| JP | 09-281078 | 10/1997 |
| WO | WO 97/46707 | 12/1997 |
| WO | WO 99/60381 | 11/1999 |
| WO | WO 00/13017 | 3/2000 |
| WO | WO 00/31518 | 6/2000 |
| WO | WO 00/58715 | 10/2000 |
| WO | WO 01/35079 A1 | 5/2001 |

OTHER PUBLICATIONS

Hebner et al., Local Tuning of Organic Light-Emitting Diode Color by Dye Droplet Application, *American Institute of Physics* (1998).

Higuchi et al., Kinetic PCR Analysis: Real-Time Monitoring Of DNA Amplification Reactions, *Bio Technology*, vol. 11, pp. 1026-1030 (1993).

Qui et al., Room Temperature Ultraviolet Emission From an Organic Light-Emitting Diode, *American Institute of Physics* (2001).

Ririe et al., Product Differentiation By Analysis of DNA Melting Curves During the Polymerase Chain Reaction *Analytical Biochemistry*, vol. 245, pp. 154-160 (1997).

Teresko, Winning Technologies: Organic Light Emitting Diode, *Industry Week*, (Dec. 11, 2000).

Tollefsrud, *Electronic Paper: Organic Light Emitting Diode*, http://komar.cs.stthomas.edu/qm425/01s/Tollefsrud2.htm (Printed Jan. 10, 2003).

Wittwer et al., The LightCycler ™: A Microvolume Multisample Fluorimeter with Rapid Temperature Control, *BioTechniques* vol. 22, No. 1, pp. 176-181 (Jan. 1997).

International Search Report, mailed Dec. 8, 2003, for International Application No. PCT/US03/15945.

Excerpts of Japanese-Language Book to Hiroki Nakayama, entitled Cellular Engineering, Separate Volume, Visual Experiment Note Series Bio Experiment Illustrated 3 New Edition, Truly Increasing PCR, Japan Shujunsha Co., Ltd. ,Aug. 1, 2000, Second Edition Third Printing, pp. 45 to 46, p. 169, Chapter 2, Basic PCR Protocols, Section 1, Setting the Reaction Temperature and Number of Cycles, Chapter 9, Actual Quantification Using PCR, sections 4-2-4 and 5, Concrete Examples of Quantitative PCR Using RI.

\* cited by examiner

OPTICAL INSTRUMENT INCLUDING EXCITATION SOURCE

CROSS-REFERENCE TO RELATED APPLICATION

The present application claims a benefit from earlier filed U.S. Provisional Patent Application No. 60/381,671, filed May 17, 2002, U.S. Provisional Patent Application No. 60/409,152, filed Sep. 9, 2002, and U.S. Provisional Patent Application No. 60/450,734, filed Feb. 28, 2003 and is a continuation-in-part of U.S. patent application Ser. No. 10/216,620, filed Aug. 9, 2002 now U.S. Pat. No. 7,008,789, which is a continuation of U.S. patent application Ser. No. 09/700,536, filed Nov. 29, 2001 now U.S. Pat. No. 6,818,437, which is is the National Stage of International Application No. PCT/US99/11088, filed May 17, 1999, which published as publication number WO 99/60381 on Nov. 29, 1999. Cross-reference is made to U.S. patent application Ser. No. 10/440,852, and to U.S. patent application Ser. No. 10/440,920, both filed May 19, 2003. All Patents, Patent Applications, and publications mentioned herein are incorporated herein in their entireties by reference.

FIELD

The present teachings relate to an instrument for detecting and measuring fluorescence, and to fluorescence measurement methods that can be used in assays based on nucleic acid sequence amplification, for example, Polymerase Chain Reaction (PCR).

BACKGROUND

A fluorometer including an array of light-emitting diode (LED) light sources in one-to-one correspondence with sample containers is described in International Publication No. WO 01/35079, which is incorporated herein in its entirety by reference. Various problems can be encountered, however, with such a system. For example, such a system can be costly for commonly used experimentation involving analysis of a 96 sample well array and would require 96 LED light sources. The use of one light source per well, can also result in photobleaching of fluorescent dyes present in samples being analyzed

SUMMARY

According to various embodiments, an optical instrument is provided. The instrument can comprise a plurality of spaced-apart reaction regions, an excitation source adapted to simultaneously illuminate two or more of the spaced-apart reaction regions, and a collimating lens disposed along an excitation beam path between the excitation source and the spaced-apart reaction regions. The excitation source can comprise a single LED, an array of a plurality of LEDs, a single laser, or an array of a plurality of lasers.

According to various embodiments, an optical instrument is provided that includes a collimating lens that focuses excitation beams radiated from a light source into discrete bundles of collimated excitation beams that can simultaneously illuminate two or more of a plurality of spaced-apart reaction regions, for example, two or more wells of a multi-well microtiter plate.

According to various embodiments, methods are provided for simultaneously illuminating two or more spaced-apart reaction regions with respective bundles of collimated excitation beams generated by a light source in combination with a collimating lens. The light source can comprise a single LED, an array of a plurality of LEDs, a single laser, or an array of a plurality of lasers. The collimating lens can comprise a single collimating lens or an array of collimating lenses.

Additional embodiments are set forth in part in the description that follows, and in part will be apparent from the description, or may be learned by practice of the various embodiments described herein.

It is to be understood that both the foregoing general description and the following detailed description are exemplary and explanatory only, and are intended to provide a further explanation of the various embodiments of the present teachings.

DESCRIPTION OF VARIOUS EMBODIMENTS

Various embodiments described herein provide an optical instrument. The instrument can include a plurality of spaced-apart reaction regions, a light source adapted to simultaneously illuminate at least two of the reaction regions with excitation radiation, and a collimating lens disposed along an excitation beam path between the light source and the reaction regions. An exemplary embodiment is shown in FIG. 1.

Figure 1:
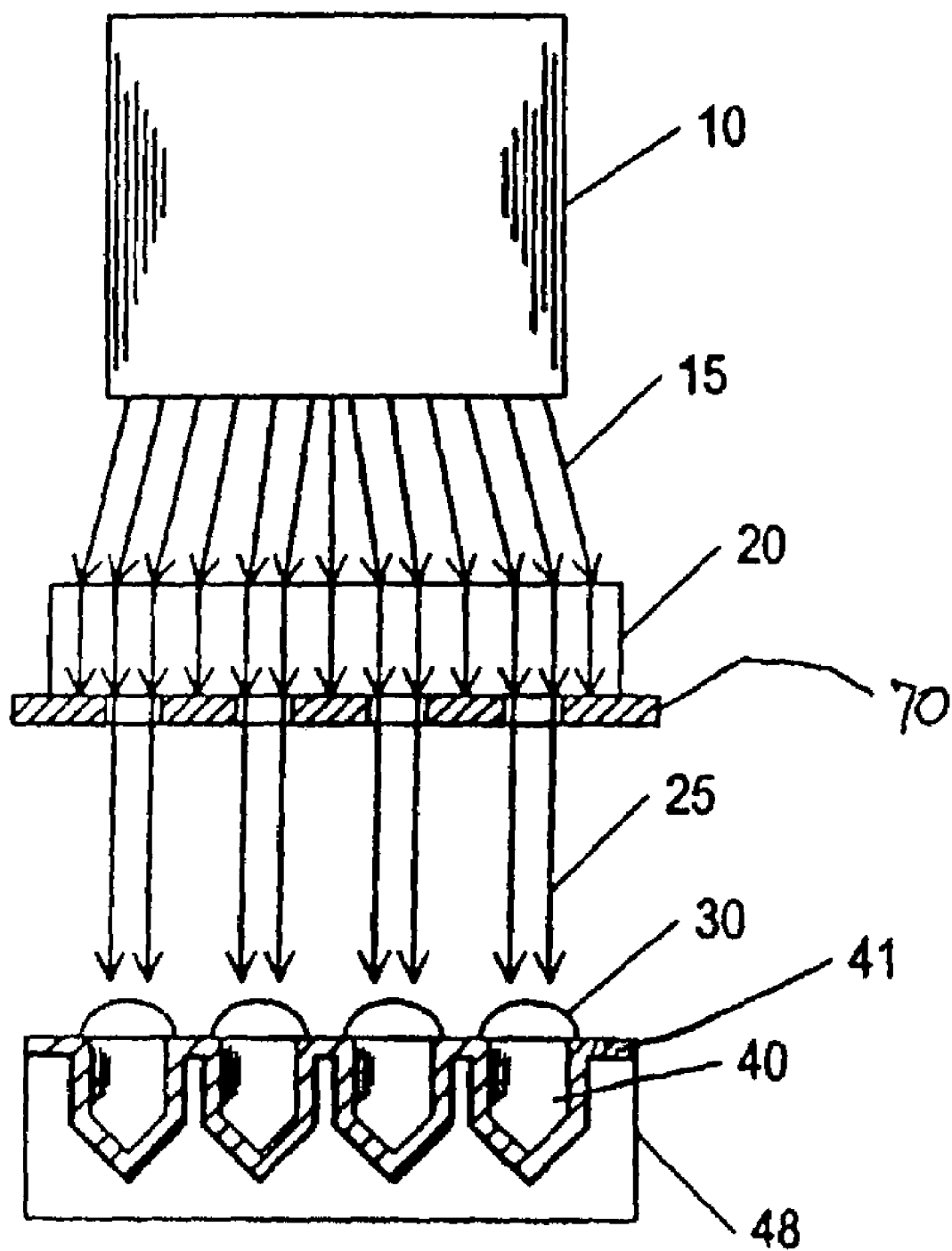
FIG. 1 is a schematic diagram of an optical pathway for an optical instrument that includes a light source and a collimating lens, and an optical pathway for illuminating a plurality of spaced-apart reaction containers, according to various embodiments.

According to various embodiments and as shown in FIG. 1, an instrument is provided for illuminating multiple spaced-apart reaction regions with an excitation source. The light source 10 can emit excitation beams 15 that can pass through a collimating lens 20. The collimating lens 20 can collimate the excitation beams such that the excitation beams emerge from the collimating lens parallel to the optical axis of the collimating lens and as discrete bundles 25 of collimated excitation beams. The bundles 25 of collimated excitation beams can impinge on a plurality of spaced-apart reaction regions 40, such that each bundle 25 of collimated excitation beams emitted by the collimating lens can impinge on a respective reaction region, for example, one of reaction regions 40 of a sample well tray 41 held by a holding assembly 48. According to various embodiments, the bundles 25 of collimated excitation beams can be focused on the respective reaction regions 40 by passage through respective focusing lenses, such as reaction region lenses 30. According to various embodiments, a mask 70 can be used with the collimating lens 20 to eliminate extraneous light such that all light passing through the mask 70 is directed toward or impinges on a respective reaction region lens 30.

Figure 2:
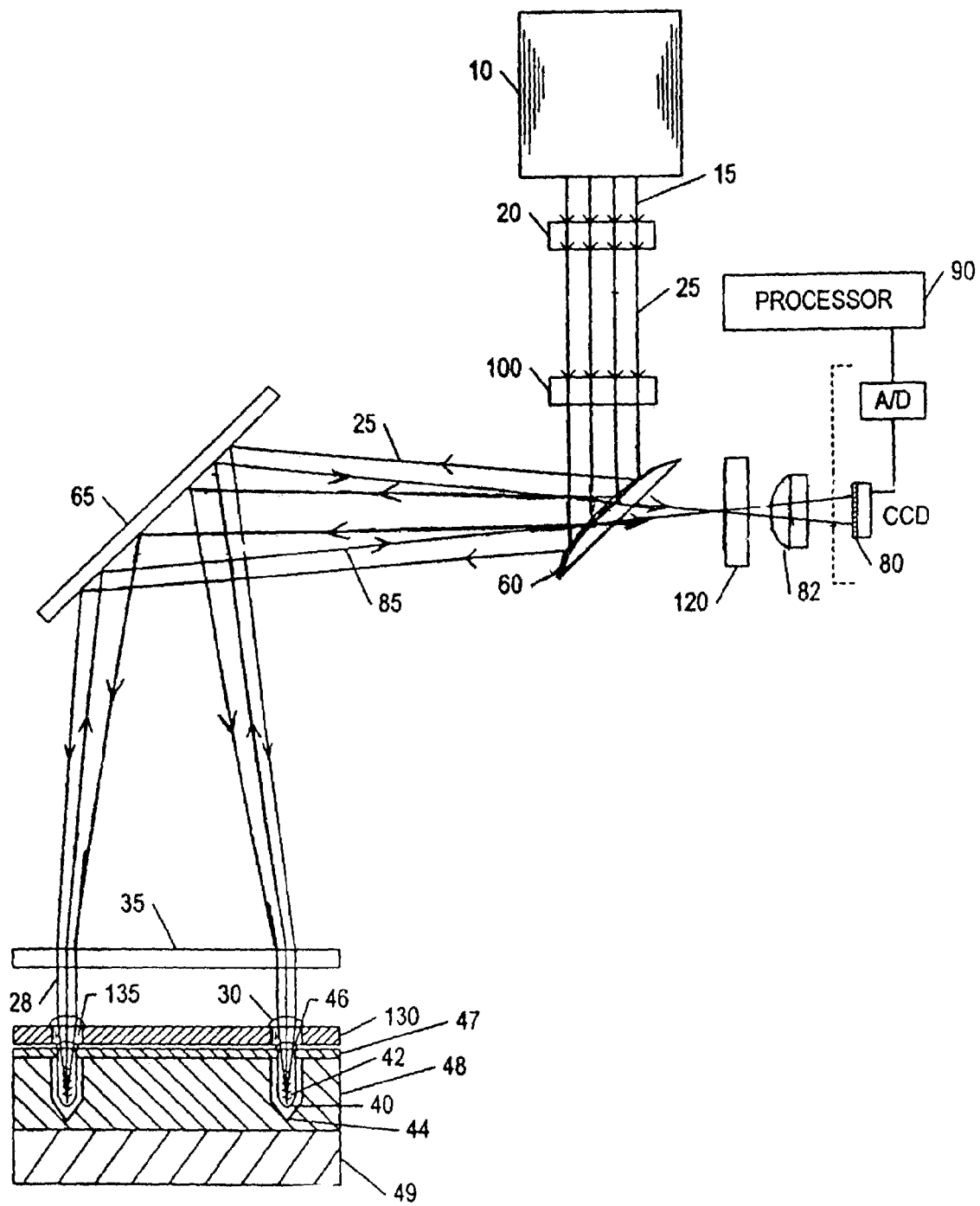
FIG. 2 is a schematic diagram of an optical instrument and an optical pathway generated by the optical instrument according to various embodiments.

FIG. 2 shows a system according to various embodiments that can include a reaction region holding assembly 48, for example, a thermal cycler block, including wells 44 for holding respective reaction regions 40, for example, vials, spaced apart from one another. The reaction regions can contain respective samples 42. The samples can be, for example, respective suspensions of ingredients for polymerase chain reaction (PCR) or other nucleic acid sequence amplification methods. If the reaction region holding assembly 48 is a thermal cycler block, the assembly 48 can include a thermal cycle controller 49 for cycling the temperature of the block through a temperature program.

Each reaction region 40 can include, for example, any chamber, vessel, container, sample well, capsule, vial, centrifuge tube, gel, capillary tube, capillary channel, or other containing, restraining, retaining, or confining device, without limitation, that is capable of retaining a sample for fluorometric analysis or illumination thereof. The reaction regions 40 can be fixed, secured, mounted, or otherwise attached or connected to, separate from, or integral with, the reaction region holding assembly 48. The holding assembly 48 can be attached or connected to, or placed on, a surface of a substrate or a holder and positioned to enable two or more reaction regions to be simultaneously illuminated by a light source. According to various embodiments wherein the reaction region is integral with the holding assembly, the holding assembly can be, for example, a purification tray, microtiter tray, multiwell tray, sample array, or like device for holding multiple samples.

The samples 42 to be analyzed can include aqueous suspensions of sample materials, for example, a "seed" sample of a target nucleic acid sequence, selected primers, nucleic acids, enzymes, buffers, and other chemicals conventionally used for PCR.

The reaction regions 40 can be heated and cooled in a predetermined cycle by electric heaters, liquid or air coolants, or a combination thereof, or by other methods known to those skilled in the art to achieve thermal cycling. The reaction regions 40 can be cycled between two temperature phases so as to affect PCR, for example. The reaction regions 40 can be held at a constant temperature for an isothermal reaction.

Spaced-apart reaction regions 40 can be, for example, conical or cylindrical vials, and can be separate from each other or can be integrally formed in a unitary tray, for example, a plastic tray. According to various embodiments, the reaction region holding assembly 48 can hold a plurality of vials, for example, 96 vials, in an array, such as an array of 12 by 8 vials. According to various embodiments, the vials or reaction regions 40 can be removed from the reaction region holding assembly 48 for preparation and/or sample loading. According to various embodiments, a plastic unitary cover, such as a cover including caps 46, can be provided to seal the vials.

Figure 7:
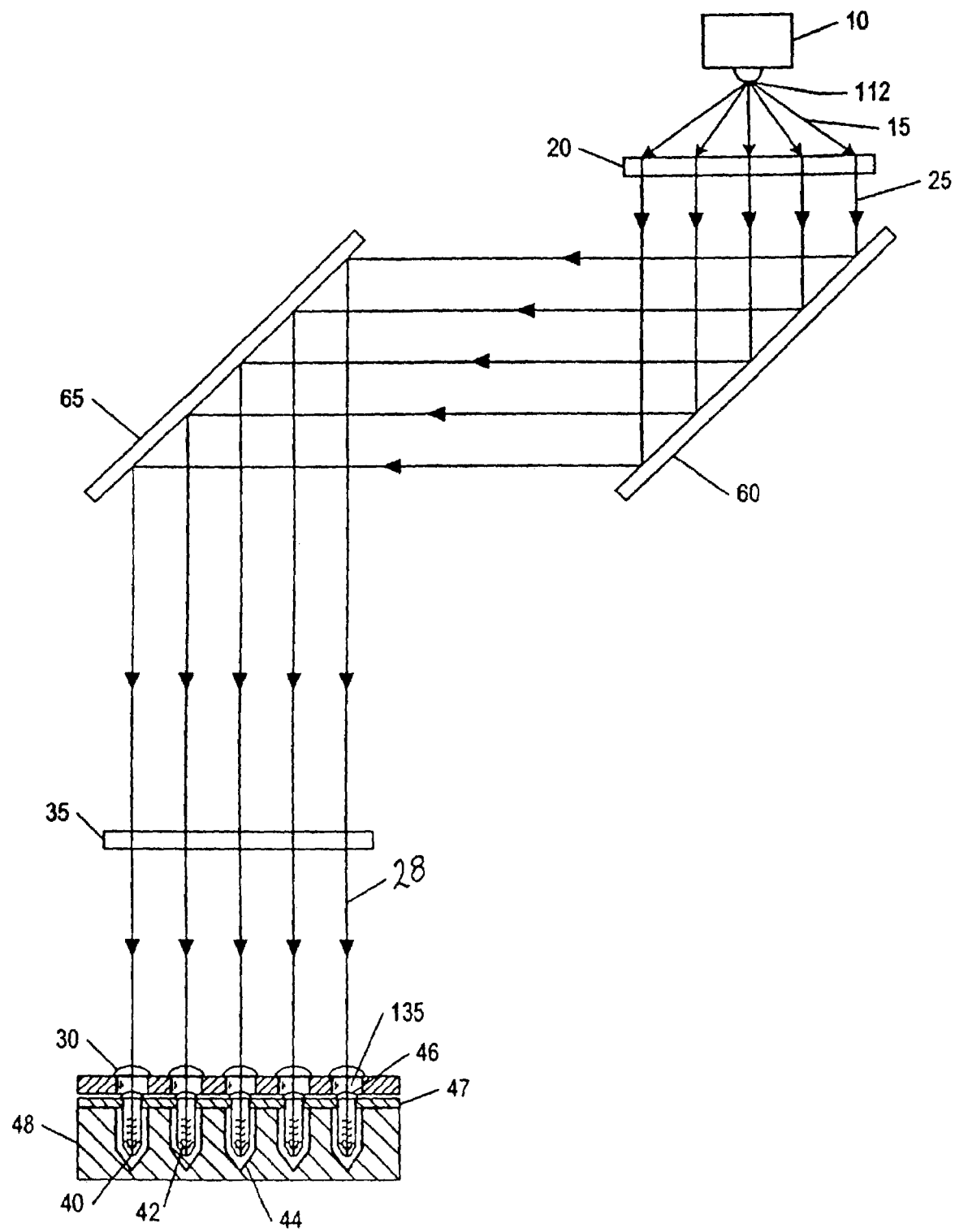
FIG. 7 is a schematic diagram of an optical instrument that includes a light source and a collimating lens, and an optical pathway the instrument generates, according to various embodiments.
Figure 8:
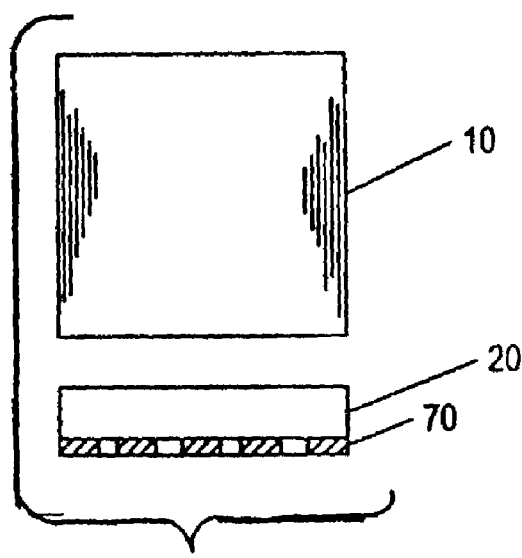
FIG. 8 is a schematic diagram of a portion of an optical instrument that includes a light source, a collimating lens, and a mask, according to various embodiments.
Figure 9:
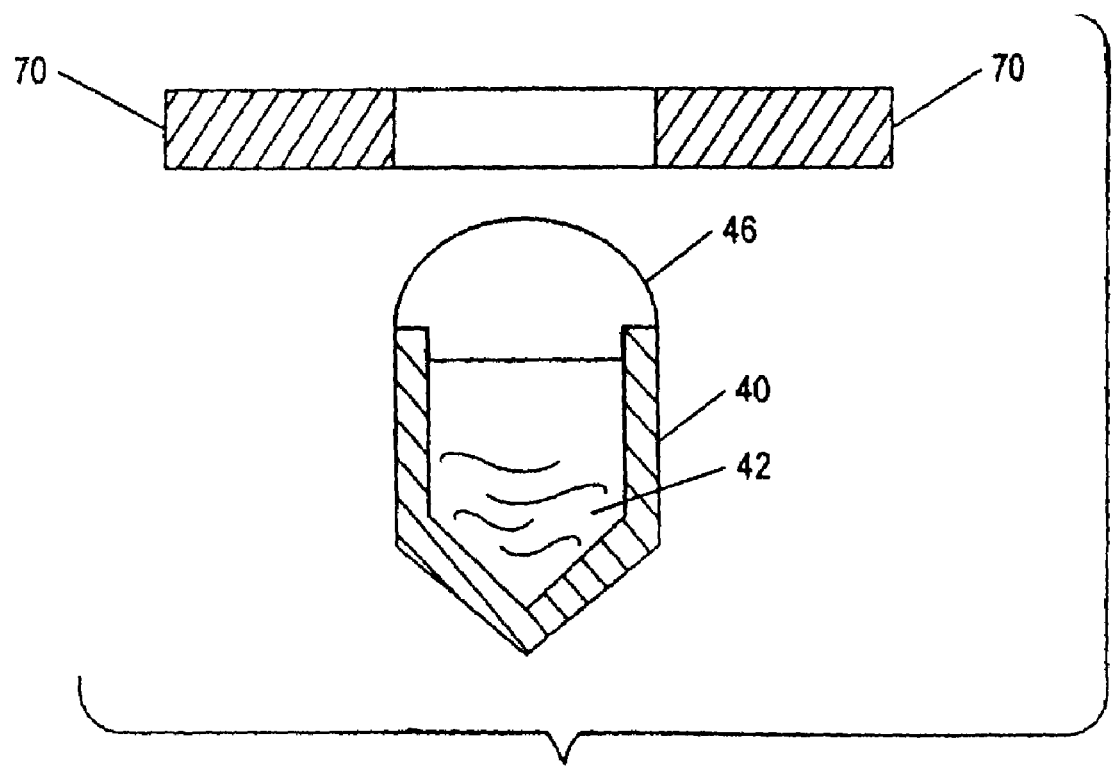
FIG. 9 is a schematic diagram of a portion of an optical instrument that includes a mask, a reaction region lens, and a reaction region, according to various embodiments.

The caps 46 for the reaction regions 40 can rest on, attach to, or seal tightly with the reaction regions 40 to prevent contamination and evaporative loss of the samples 42 in the reaction regions 40. Other methods and instruments can instead or also be used for this function, such as disposing oil such as mineral oil on the sample surface, in which case caps may not be needed. If used, the caps 46 can be transparent to light utilized in the instrument. The caps 46 can be convex, for example, facing upwardly. According to various embodiments, the caps 46 can be a film or a heat seal cover. According to various embodiments and as shown in FIG. 2, convex, upwardly facing caps 46 can function as reaction region lenses to focus respective bundles 28 of collimated excitation beams into a sample 42 in a respective reaction region 40. According to various embodiments, each cap 46 can fit snugly on or in each respective vial 40 such that the cap 46 when fit into or onto vial 40 can support the weight of vial 40 suspended from the cap 46. According to various embodiments wherein vial 40 is suspended from cap 46, as shown in FIG. 9, the cap can have a mushroom-like shape, having a convex top and a narrower base protruding below the top such that the narrower base can fit snugly into vial 40. The cap 46 supporting the vial 40 can rest on a platform 47, as shown in FIGS. 2 and 7, wherein the platform includes through holes for passage of vials 40 through the platform such that caps 46 rest on platform 47 while vials 40 are suspended from caps 46 and extend through platform 47. According to various embodiments, a plurality of caps 46 can be formed as a single sheet such that the sheet can be laid over a plurality of reaction regions or vials 40.

According to various embodiments, a monitoring instrument can be mounted over the reaction region holding assembly 48 containing the reaction regions 40. The instrument can be removable or can swing away for access to the reaction regions 40.

As shown in FIG. 2, for example, the instrument can include a platen 130 that rests over the caps 46 or, if no caps are used, that rests directly over the reaction regions 40. The platen 130 can be aluminum and can include an array of holes 135 aligned with reaction regions 40, with each hole having a diameter that is about the same as the top diameter of the reaction region. If caps 46 are used, the platen 130 can have its temperature maintained by a film heater or other instrument to prevent condensation from forming under the caps 46. The heating of the platen, however, should not interfere with the reaction, such as DNA replication, in the reaction regions 40.

An exemplary method to prevent condensation is to maintain the platen 130 at a slightly higher temperature than the highest sample temperature that the reaction region holding assembly 48 reaches.

According to various embodiments and as depicted in FIG. 2, above each reaction region 40, a focusing lens such as a reaction region lens 30 can be positioned having a focal point that is approximately centered in a respective sample 42 in a respective reaction region 40. A focusing lens 35, for example, an objective lens or a Fresnel lens, can be placed above reaction region lens 30 to provide, for example, a telecentric optical system. The terms "focusing lens" and "reaction region lens" used throughout this disclosure can, according to various embodiments, be interchangeable in that a reaction region lens, a focusing lens, or both can be present according to various embodiments. Each focusing lens 35 and each reaction region lens 30 can include two or more lenses that can together affect a desired focus, thus the word "lens" herein includes such multiplicities. A convex, upwardly facing cap of a reaction region can function, for example, as a reaction region lens. According to various embodiments, a neutral density pattern (not shown) to correct inconsistencies in illumination and imaging can be mounted on or in proximity to the focusing lens or reaction region lens, for example, to attenuate light in the center of the image field.

A fluorescent marker or dye in a sample in a reaction region can emit light at an emission frequency when excited by an excitation beam of the appropriate wavelength. The emitted light can be passed as emission beam 85 to a detector 80. According to various embodiments and as shown in FIG. 2, emission beam 85 can pass through a reaction region lens 30 and/or focusing lens 35 to a detector 80. A fold mirror 65 can be optionally mounted at 45°, or at any other suitable angle for convenient packaging of the instrument. The fold mirror 65 can be omitted, or other such folding optics can be used instead of or in addition to the fold mirror. According to various embodiments, emission beam 85 can be reflected by fold mirror 65 toward a transition filter 60, such as a long pass filter or beamsplitter. Transition filter 60 can pass or reflect an emission beam 85 to detector 80. According to various embodiments, transition filter 60 can include a curved surface, as shown in FIG. 2.

One or more of reaction region lenses 30, focusing lenses 35, and caps 46 can provide a primary focusing system for focusing respective bundles of excitation beams into reaction region 40 and/or for focusing emission beams 85 toward a detector 80. According to various embodiments, focusing lens 35 can be omitted so that the focusing system includes reaction region lens 30, or vice versa. According to various embodiments, a plurality of reaction region lenses can form a reaction region lens array, wherein each reaction region lens can correspond to a separate reaction region. The reaction region lenses can be disposed between the collimating lens 20 and the reaction region such that each bundle of collimated excitation beams from the collimating lens impinges on a respective reaction region lens and can be focused on a sample in a respective reaction region. According to various embodiments, one or more of the focusing lenses 35, the reaction region lenses 30, and the caps 46 can focus an emission beam 85 on the detector 80.

According to various embodiments, a focusing lens and/or a reaction region lens can be located between a collimating lens and a reaction region, between a transition filter and a reaction region, between a mirror and a reaction region, or between a second field lens and a reaction region. If used in combination with a reaction region lens, a focusing lens can be positioned between a reaction region lens and collimating lens, transition filter, mirror, or second field lens.

To filter the bundles of collimated excitation beams, an excitation filter 100 can be disposed between the collimating lens 20 and the transition filter 60, as shown in FIG. 2. Excitation filter 100 can pass light having the excitation frequency for the markers or dyes used in the samples, and can substantially block light having the emission frequency.

According to various embodiments as shown in FIG. 2, an emission filter 120 can be disposed between transition filter 60 and detector 80. Emission filter 120 can be disposed between transition filter 60 and detector lens 95 in front of detector 90. The emission filter 120 can pass emission beam 85 having the emission frequency emitted from the illuminated samples and can substantially block light having the excitation frequency.

According to various embodiments and as shown in FIG. 2, excitation filter 100 and transition filter 60 together constitute a first system disposed to receive bundles of collimated excitation beams 25 having the excitation frequency from collimating lens 20. According to various embodiments, emission filter 120 and transition filter 60 together constitute a second system disposed to receive emission beams 85 from the focusing lens 35 and/or reaction region lens 30 so as to pass emission beams 85 at an emission frequency to detector 80. According to various embodiments, the excitation and emission filters can be omitted, and the first system can include a transition filter 60 that reflects or passes bundles of collimated excitation beams 25, and the second system can include a transition filter 60 that passes or reflects, respectively, emission beams 85 to the detector 80.

Figure 3:
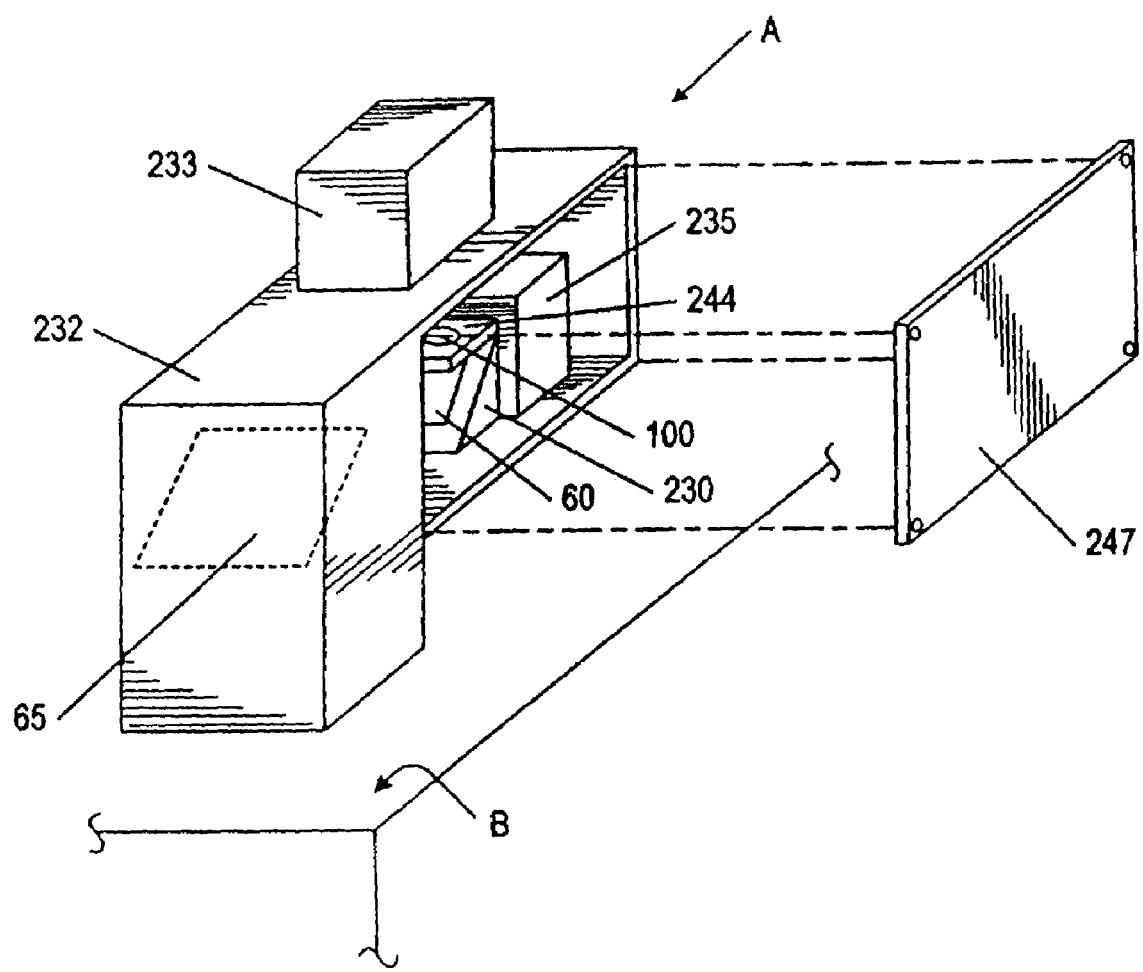
FIG. 3 is a perspective view of an optical instrument for providing the optical pathway shown in FIG. 2, with a side panel of the instrument removed.

According to various embodiments, the transition filter 60, excitation filter 100, and emission filter 120 can be affixed in a module 230 as shown in FIG. 3. These elements can be associated with a selected primary dye used in the samples. The module can be removable from a housing 232 of the instrument A for replacement with another module capable of containing a different filter, excitation filter, and emission filter associated with another selected primary dye. The instrument A can include a light source subhousing 233 and a detector or camera subhousing 235. As shown in FIG. 3, the transition filter 60 can be located in instrument A such that the transition filter 60 is at a 45° angle with respect to plane B of the instrument. Other suitable angles of placement of the transition filter with respect to plane B can be used.

Figure 4:
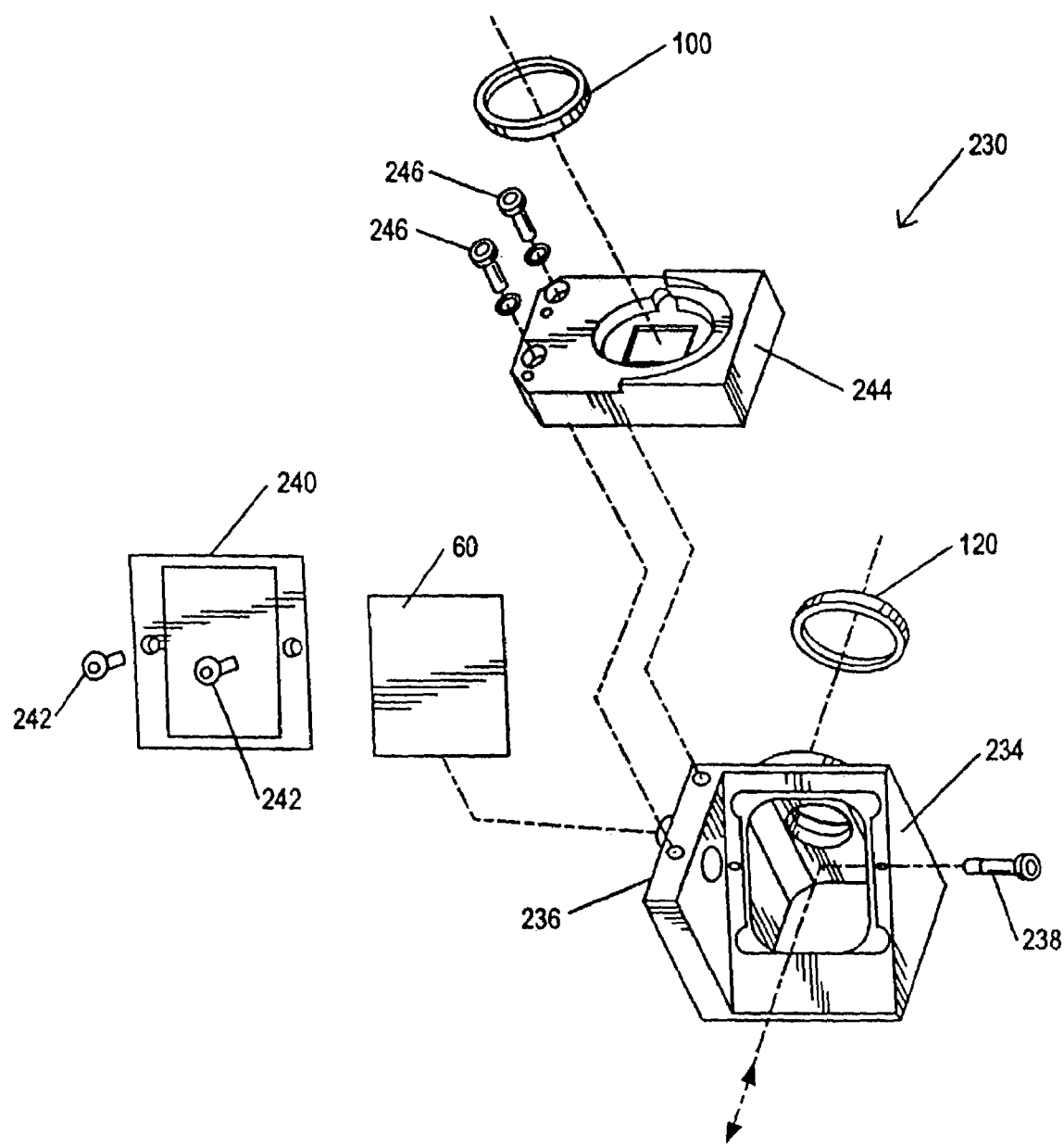
FIG. 4 is an exploded perspective view of the optical instrument shown in FIG. 3.

According to various embodiments and as shown in FIG. 4, a changeable module 230 of an instrument A, as shown in FIG. 3, can include a mounting block 234 having a flange 236 that can be affixed to the housing 232 with a single screw 238. Transition filter 60 can be held at about 45°, or any other suitable angle, in mounting block 234 with a frame 240 and screws 242. Emission filter 120 can be mounted, for example, with glue, by frictional engagement, snap-fit, or the like, into mounting block 234. Excitation filter 100 can be mounted similarly into mounting member 244, which in turn can be held by screws 246 to mounting block 234. With the module 230 in place, the instrument A can be closed by attaching side plate 247 as shown in FIG. 3, for example, with screws. Optionally, positioning pins (not shown) can be used for repeatable alignment. A replacement module can include the same or similar mounting block and associated components but with a different transition filter, mask, excitation filter, and/or emission filter.

Figure 5:
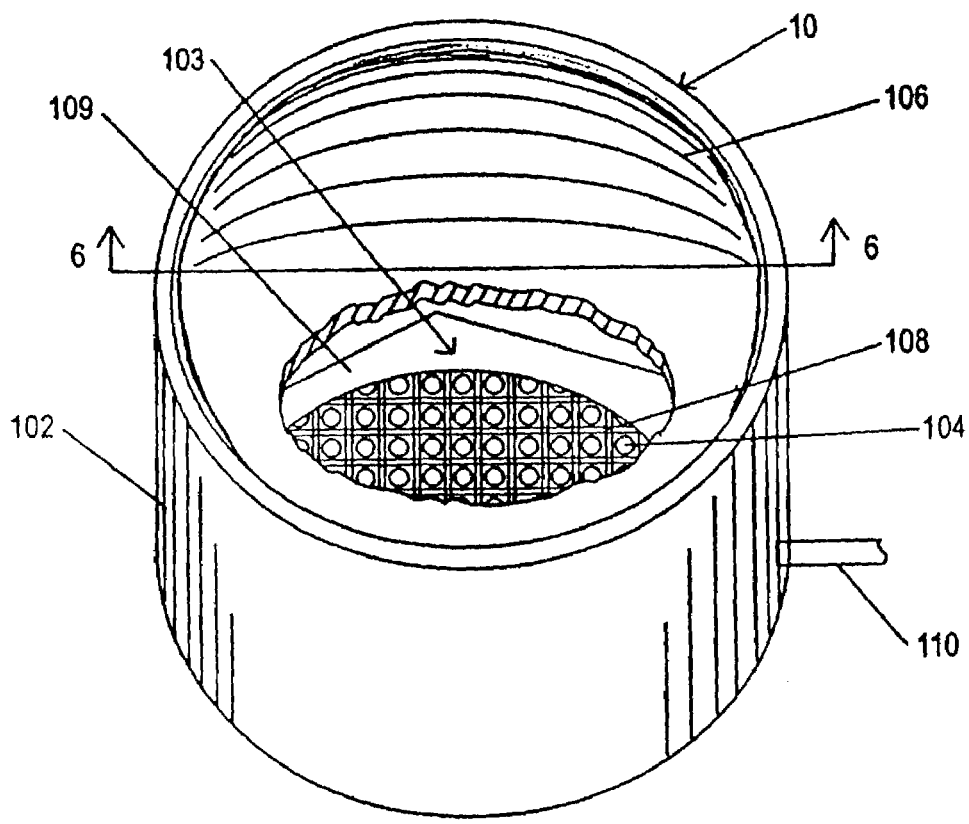
FIG. 5 is a perspective view of an excitation source that includes an array of light sources used according to various embodiments.
Figure 6:
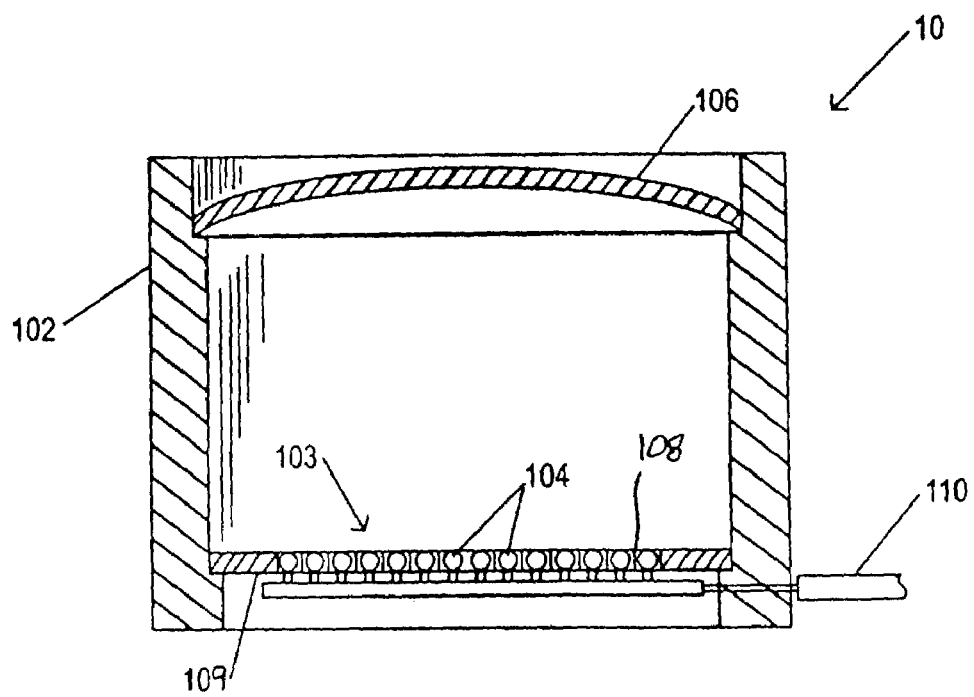
FIG. 6 is a cross-sectional view of the excitation source shown in FIG. 5 taken along line 6-6 in FIG. 5.

The light source 10 that can emit excitation beams 15 can be a single light source or an array or bundle of light sources. According to various embodiments and as shown in FIGS. 5 and 6, the light source 10 can include an array 103 of individual light sources 104 secured in a substrate 108. The substrate 108 can be made from any material that can withstand the heat emitted from the light source. For example, metal and plastics can be used for substrate 108. The substrate 108 can be capable of mounting into a body 102, as shown in FIG. 6. A platform 109 can be provided for mounting the light sources 104 and substrate 108 in the body 102. The array of individual light sources 104 can be secured within body 102 by suitable devices such as rubber bands, tabs, glue, or other means without the use of substrate 108. The body 102 can include a lens 106 as shown in FIGS. 5 and 6. According to various embodiments, the lens 106 is located spaced from the array 103 of individual light sources 104. Light source 10 can also include power source 110 capable of illuminating each individual light source 104, simultaneously, individually, sequentially, in groups, in rows, or in other configurations or orders of illumination. Groups of individual colors from the array can sequentially be illuminated. The light source array can generate excitation beams of light referred to herein as excitation beams or area light excitation beams.

According to various embodiments, groups of predetermined numbers of light sources 104 can emit respective wavelengths such that the different groups of light sources emit different excitation frequencies. The groups can each be arranged as rows of individual light sources 104 or can include a plurality of light sources of a first excitation beam wavelength homogeneously distributed throughout the array along with the light sources of the other excitation beam wavelengths. The wavelength or wavelengths emitted from each group of light sources can correspond to a particular excitation frequency for a marker or dye used in one or more of the samples. A controller, capable of powering one or more of the individual light sources 104 or groups of light sources in the array 103, can power the light sources of a group having a particular wavelength simultaneously or independently of the light sources of the other groups. Each group of light sources powered by the controller can provide excitation beams that illuminate at least two of the plurality of reaction regions simultaneously, and can cause a respective marker or dye to fluoresce.

According to various embodiments, and as shown in FIG. 7, the light source 10 can include a single light source 112. Excitation beams emitted from the light source 112 diverge from the light source 112 at an angle of divergence. The angle of divergence can be, for example, from about 5° to about 75° or more. The angle of divergence can be substantially wide, for example, greater than 45°, yet can be efficiently focused by the use of a collimating lens 20. According to various embodiments, bundles of collimated excitation beams 25 that have passed through collimating lens 20 can be reflected off of a long pass filter 60 in a direction toward fold mirror 65. Bundles of collimated excitation beams reflected from fold mirror 65 can pass through a focusing lens 35, for example, a Fresnel lens. According to various embodiments, each of the bundles of collimated excitation beams can be focused by a respective reaction region lens 30 before illuminating a respective sample 42 in the corresponding reaction region 40. In the embodiment shown in FIG. 7, the reaction regions are individual vials in a series of wells in a tray 48.

According to various embodiments, a light source can contain one Light Emitting Diode (LED) or an array of LEDs. According to various embodiments, each LED can be a high power LED that can emit greater than or equal to 1 mW of excitation energy. In various embodiments, a high power LED can emit at least 5 mW of excitation energy. In various embodiments wherein the LED can emit at least 5 mW of excitation energy, a cooling device such as, but not limited to, a heat sink or fan can be used with the LED. An array of high-powered LEDs can be used that uses only about 10 watts of energy or less, depending on the power of each LED and the number of LEDs in the array. The use of an LED array can result in a significant reduction in power requirement over other light sources, such as, for example, a 750 watt halogen light source. Exemplary LED array sources are available, for example, from Stocker Yale as LED AREALIGHTS.

According to various embodiments, the light source can be a Light Emitting Diode (LED). The LED can include an Organic Light Emitting Diode (OLED), or a Thin Film Electroluminescent Device (TFELD). The LED can include a phosphorescent OLED (PHOLED). If an OLED is used, the OLED can have any of a variety of sizes, shapes, and/or wavelengths. The OLED can be a low power consumption device. Examples of OLEDs in various configurations and wavelengths are described in, for example, U.S. Pat. No. 6,331,438 B1, which is incorporated herein in its entirety by reference. The OLED can include a small-molecule OLED and/or a polymer-based OLED also known as a Light-Emitting Polymer (LEP). An OLED can be used that is a small-molecule OLED deposited on a substrate. An OLED can be used that is deposited on a substrate. An OLED can be used that is deposited on a surface by vapor-deposition technique. An LEP can be used that is deposited by solvent coating.

According to various embodiments, an OLED is used and can be formed from one or more stable, organic materials. The OLED can include one or more carbon-based thin films and the OLED can be capable of emitting light of various colors when a voltage is applied across the one or more carbon-based thin films.

According to various embodiments, the OLED can include a film that is located between two electrodes. The electrodes can be, for example, a transparent anode and/or a metallic cathode. The OLED film can include one or more of a hole-injection layer, a hole-transport layer, an emissive layer, and an electron-transport layer. The OLED can include a film that is about one micrometer in thickness, or less. When an appropriate voltage is applied to the film, the injected positive and negative charges can recombine in the emissive layer to produce light by means of electroluminescence. The amount of light emitted by the OLED can be related to the voltage applied through the electrodes to the thin film of the OLED. Various materials suitable for fabrication of OLEDs are available, for example, from H.W. Sands Corp. of Jupiter, Fla. Various types of OLEDs are described, for example, in U.S. Pat. No. 4,356,429 to Tang, U.S. Pat. No. 5,554,450 to Shi et al., and in U.S. Pat. No. 5,593,788 to Shi et al., all of which are incorporated herein in-their entireties by reference.

According to various embodiments, an OLED is used and can be produced on a flexible substrate, on an optically clear substrate, on a substrate of an unusual shape, or on a combination thereof. Multiple OLEDs can be combined on a substrate, wherein the multiple OLEDs can emit light at different wavelengths. Multiple OLEDs on a single substrate or multiple adjacent substrates can form an interlaced or a non-interlaced pattern of light of various wavelengths. The pattern can correspond to, for example, a sample reservoir arrangement. One or more OLEDs can form a shape surrounding, for example, a sample reservoir, a series of sample reservoirs, an array of a plurality of sample reservoirs, or a sample flow path. The sample path can be, for example, a channel, a capillary, or a micro-capillary. One or more OLEDs can be formed to follow the sample flow path. One or more OLEDs can be formed in the shape of a substrate or a portion of a substrate. For example, the OLED can be curved, circular, oval, rectangular, square, triangular, annular, or any other geometrically regular-shape. The OLED can be formed as an irregular geometric shape. The OLED can illuminate one or more sample reservoirs, for example, an OLED can illuminate one, two, three, four, or more sample reservoirs simultaneously, or in sequence. The OLED can be designed, for example, to illuminate all the wells of a corresponding multi-well array.

According to various embodiments, one or more excitation filters can be incorporated into the OLED substrate, thus eliminating additional equipment and reducing the amount of space needed for an optical system. For example, one or more filters can be formed in a layer of a substrate including one or more OLEDs and a layer including a sample flow path. The wavelength emitted by the OLED can be tuned by printing a fluorescent dye in the OLED substrate, as taught, for example, by Hebner et al. in "Local Tuning of Organic Light-Emitting Diode Color by Dye Droplet Application," APPLIED PHYSICS LETTERS, Vol. 73, No. 13 (Sep. 28, 1998).

According to various embodiments, the light source can be a Solid State Laser (SSL). The SSL can produce monochromatic, coherent, directional light, and can provide a narrow wavelength of excitation energy. The SSL can use a lasing material that is distributed in a solid matrix, in contrast to other lasers that use a gas, dye, or semiconductor, lasing source material. Examples of solid state lasing materials and corresponding emission wavelengths can include, for example: Ruby at about 694 nm; Nd:Yag at about 1064 nm; Nd:YVO4 at about 1064 nm and/or about 1340 nm and which can be doubled to emit at about 532 nm or about 670 nm; Alexandrite at from about 655 nm to about 815 nm; and Ti:Sapphire at from about 840 nm to about 1100 nm. According to various embodiments, other solid state lasers known to those skilled in the art can also be used, for example, laser diodes. The appropriate lasing material can be selected based on the fluorescing dyes used or the excitation wavelength required.

If a SSL is used, the laser can be selected to closely match the optimum excitation wavelength or wavelength range of a fluorescent dye. The operating temperature of the system can be considered in selecting an appropriate SSL. The operating temperature can be changed to affect the emitted wavelength of the SSL. The light source for the laser can be any source as known to those skilled in the art, for example, a flash lamp. Useful information about various solid state lasers can be found, for example, at www.repairfaq.org/sam/lasersl.htm. Examples of solid state lasers used in various systems for identification of biological materials are discussed in U.S. Pat. No. 5,863,502 to Southgate et al. and U.S. Pat. No. 6,529,275 B2 to Amirkhanian et al.; both of which are incorporated herein in their entireties by reference.

According to various embodiments, various types of light sources can be used singularly, or in combination with other light sources. One or more OLEDs can be used with, for example, one or more non-organic LEDs, one or more solid state lasers, one or more halogen light sources, or a combination thereof.

According to various embodiments, a light source can be used to provide excitation beams to irradiate a sample solution containing one or more dyes. For example, two or more excitation beams having the same or different wavelength emissions can be used such that each excitation beam excites a different respective dye in the sample. The excitation beam can be aimed from the light source directly at the sample, through a wall of a sample container containing the sample, or can be conveyed by various optical systems to the sample. An optical system can include one or more of, for example, a mirror, a beam splitter, a fiber optic, a light guide, and/or a combination thereof.

According to various embodiments, one or more filters, for example, a bandpass filter, can be used with a light source to control the wavelength of an excitation beam. One or more filters can be used to control the wavelength of an emission beam emitted from an excited or other luminescent marker. One or more excitation filters can be associated with a light source to form the excitation beam. One or more filters can be located between the one or more light source and a sample. One or more emission filters can be associated with an emission beam from and/or wavelength or wavelength range of an excited marker or dye. One or more filters can be located between the sample and one or more emission beam detectors.

According to various embodiments, a collimating lens 20 is used to receive and direct excitation light beams 15 from a light source 10 and to collimate the excitation light beams such that the light beams originating from the point on the light source that is intersected by the optical axis of the collimating lens can emerge from the collimating lens parallel to the optical axis of the collimating lens. According to various embodiments, the collimating lens can be located one focal length away from the light source. According to various embodiments, the collimating lens can include a plurality of collimating lenses in the form of a collimating lens array.

According to various embodiments, one collimating lens 20 is provided for each light source 10. The collimating lens 20 can receive excitation light beams 15 from one light source 10 and can collimate the excitation light beams 15 such that two or more discrete bundles 25 of collimated excitation beams are produced, wherein each discrete bundle 25 of collimated excitation beams is of the same wavelength but of less energy than the initial excitation light beams 15 entering the collimating lens. According to various embodiments, each collimating lens can form four discrete bundles of collimated excitation beams from one excitation source. The collimating lens can be any material known to receive and collimate light. According to various embodiments, the collimating lens can be a Fresnel lens or a molded glass sphere. "Collimating lens" as referenced herein can include a collimating lens system including, for example, a collimating lens, a mask, a filter, or a combination thereof.

According to various embodiments, and as depicted in FIGS. 2 and 7, a transition filter 60, for example, a long pass filter, a bandpass filter, or a multiple notch filter, can be disposed to receive one or more bundles 25 of collimated excitation beams from the collimating lens 20. The transition filter 60 can be a dichroic reflector positioned at an angle, for example, 45°, to reflect bundles 25 of collimated excitation beams emitted from the light source 10. The reflected light can then illuminate at least two of the reaction regions with respective bundles 25 of collimated excitation beams such that dye molecules in respective samples of the reaction regions 40 can fluoresce at an emission frequency and produce emission beams. According to various embodiments, the transition filter 60 can pass emitted light having the emission frequency. Such a filter can utilize optical interference layers to provide a desired frequency response.

According to various embodiments as shown in FIGS. 2 and 7, and with any of the light sources described herein, transition filter 60 can be positioned so that it can reflect the bundles of collimated excitation beams 25 to fold mirror 65. The bundles of collimated excitation beams 25 can be reflected from the transition filter 60 as bundles of collimated excitation beams having the excitation frequency. As shown in FIG. 2, transition filter 60 can include a curved surface which causes the reflected excitation beams to diverge upon reflection. As shown in FIGS. 2 and 7, the bundles of collimated excitation beams 25 can be reflected off fold mirror 65 toward the respective reaction regions 40. The reflected bundles 25 of collimated excitation beams can be focused by focusing lens 35 to form respective bundles 28 that can be focused by the respective reaction region lenses 30 into samples in the respective reaction regions 40.

According to various embodiments, and as shown in FIGS. 2 and 7, a mirror 65 can be located between the collimating lens and the plurality of reaction regions. According to various embodiments including one or more field lens, the mirror can be located between a first field lens and a second field lens to direct the bundles of collimated excitation beams from the first field lens toward the second field lens. According to various embodiments, a mirror 65 can be located in an excitation beam path between a light source and a reaction region. According to various embodiments, a mirror can be located in an excitation beam path between one or more light source and two or more reaction regions. A mirror can be located between a collimating lens or a filter and a focusing lens, reaction region lens, or reaction region.

According to various embodiments, a mask 70, as shown in FIGS. 1, 8, 9, 10, 12, 13, and 16, can be provided after the collimating lens such that a special irradiance profile that is a scaled copy of the spaced-apart reaction regions can be created. The mask can eliminate unwanted excitation beams from impinging on the spaced-apart reaction regions. Mask 70 can be used to remove extraneous excitation light such that the bundles of collimated excitation beams 25 corresponding to reaction regions 40 are passed through mask 70, and other light is blocked. According to various embodiments, the mask can be optically opaque. According to various other embodiments, the mask can be anodized aluminum. Methods and materials for creating such a mask are known to practitioners in the art. An OLED with the shape of the unmasked region could be used.

According to various embodiments, a mask 70 can be located before a reaction region lens or reaction region lens array, as shown in FIG. 9. The mask can eliminate unwanted excitation beams from passing through a reaction region lens to a respective reaction region. The mask can eliminate unwanted emission beams or extraneous light from passing through a reaction region lens to a detector, minimizing signal noise.

Figure 10:
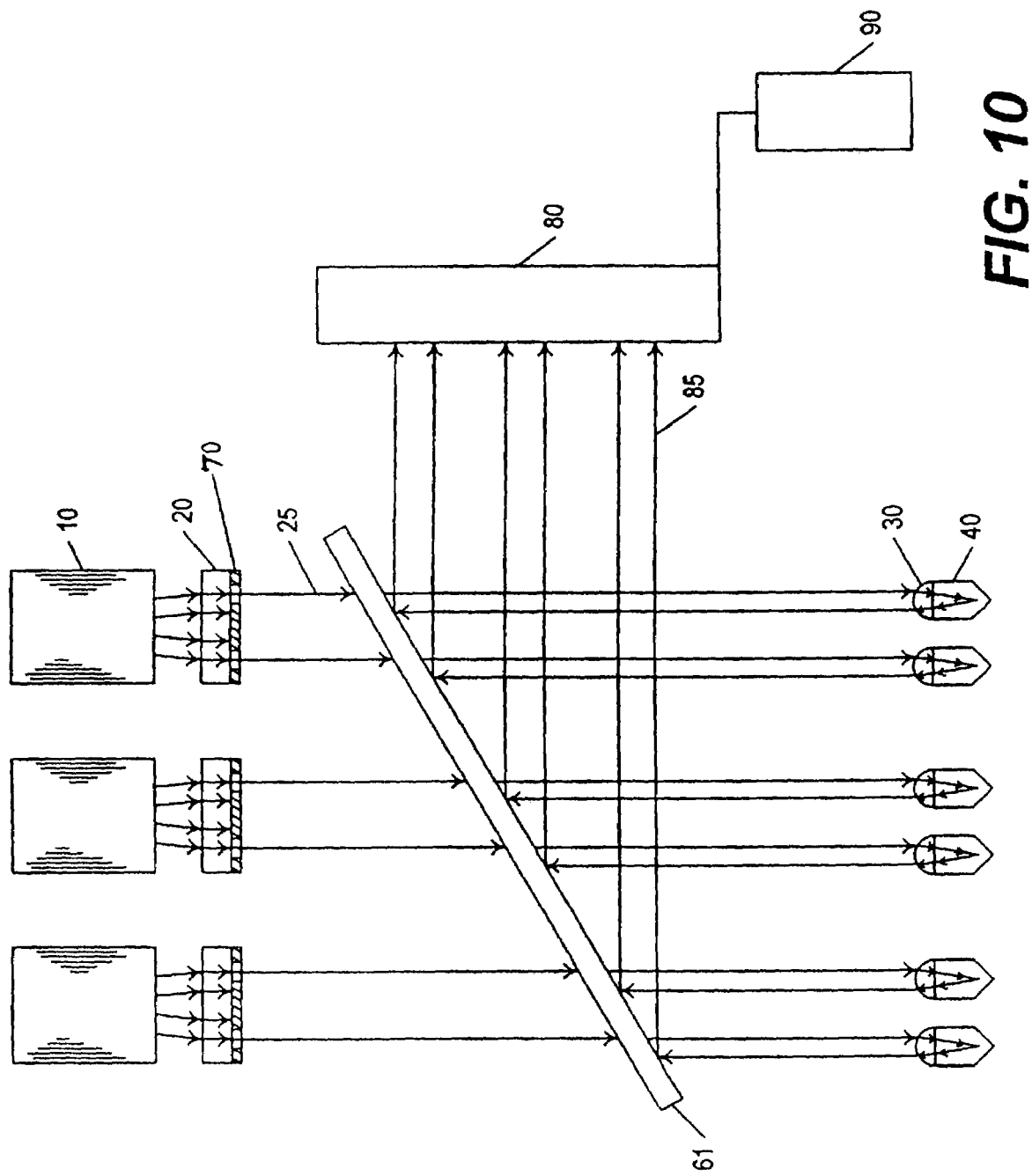
FIG. 10 is a schematic diagram of an optical, and the optical pathway generated by the optical instrument, according to various embodiments.
Figure 11:
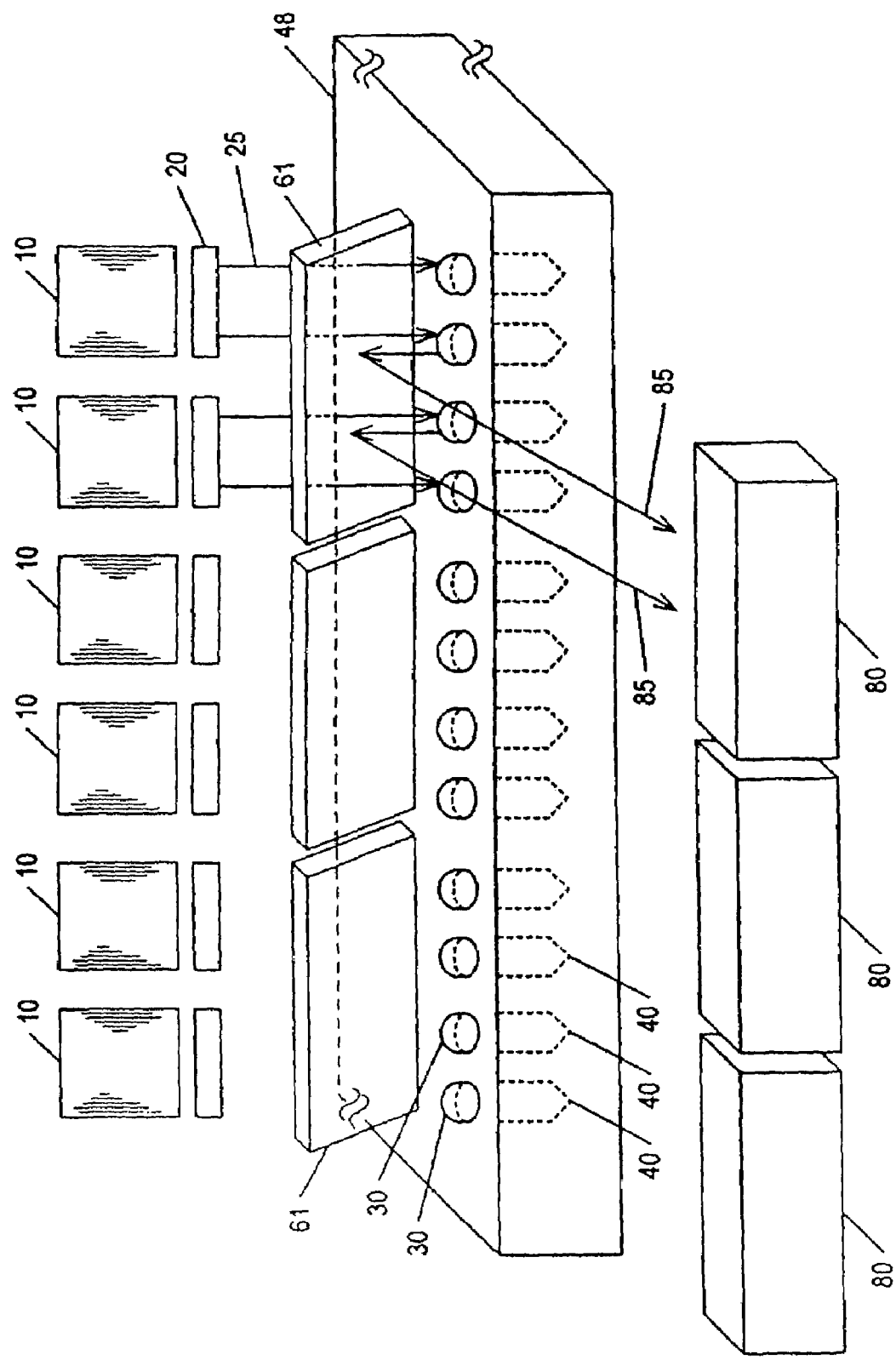
FIG. 11 is a perspective view of an optical instrument, and the optical pathway generated by the optical instrument, according to various embodiments.
Figure 12:
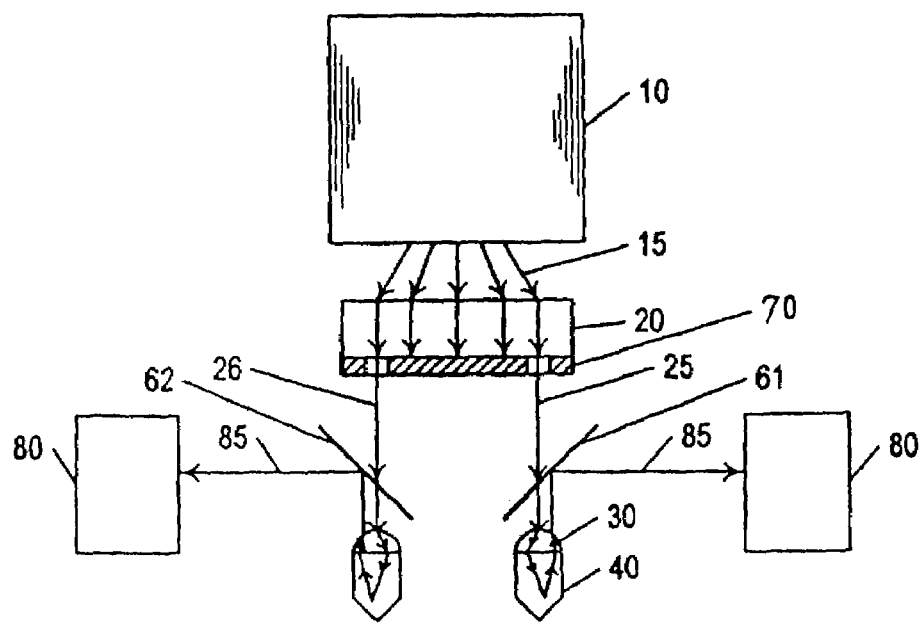
FIG. 12 is a schematic view of the optical instrument of FIG. 4 and an optical pathway generated by the optical instrument.

According to various embodiments, as shown in FIGS. 10-12, one or more transition filter 61, 62 such as, for example, a longpass filter, a short pass filter, a beamsplitter, a prism, or a diffraction grating, can be located between the collimating lens 20 and the plurality of reaction regions 40. According to various embodiments, the transition filter can be a long pass, bandpass, or multiple notch filter.

According to various embodiments, as shown in FIGS. 10-12, transition filters 61, 62 can pass bundles of collimated excitation beams 25, 26 and reflect emission beams 85 using the exemplary arrangements shown including the light source 10 and detector 80. According to various embodiments, transition filters 61 and/or 62 can individually be positioned at a 45° angle or at angles other than 45°. Although transition filters 61 and 62 can split the optical paths of the bundles of collimated excitation beams 25, 26 from the emission beam 85, other variations that achieve such a result are also suitable and can be used. For example, it can be desirable to minimize or eliminate the light source light reaching detector 80, and a dichroic long pass filter used as transition filters 61 and 62 can be used to achieve this minimization. According to various embodiments, a non-dichroic long pass filter, a 50/50 beamsplitter, a multiple notch beamsplitter can be used for one or both of transition filters 61 and 62.

According to various embodiments, a transition filter can be positioned such that the filter is located along an excitation beam path between a light source and a single reaction region. According to various other embodiments, a transition filter 61, 62 can be located between one or more light source and two or more reaction regions, as shown, for example, in FIGS. 10 and 11. According to various embodiments, the transition filter 61, 62 can be located in an excitation beam path between a collimating lens and a focusing lens, a reaction region lens, or a reaction region. According to various embodiments, the transition filter 61, 62 can be located in an emission beam path between a reaction region, reaction region lens, or focusing lens, and a detector.

According to various embodiments, a light source can emit excitation beams towards multiple reaction regions in one row of reaction regions, or in two or more rows of reaction regions. For example, each light source in FIG. 11 can illuminate reaction regions in one row. According to various embodiments, each light source can illuminate two reaction regions in two or more adjacent rows.

According to various embodiments, the sample can contain a fluorescent dye or marker that fluoresces, for example, when in the presence of a target nucleic acid sequence. Fluorescent dye probes can be used. Other dyes that have similar characteristics can be used. Intercalating dyes, reporter dyes, free-floating dyes, and other dyes can be used. The samples can also contain an additional, passive dye that can serve as a reference or control.

If a reference dye is included, it can include, for example, of a nucleic acid sequence labeled with a Rhodamine and/or Fluorescein dye or derivative thereof. An example of a suitable reference dye is ROX dye available from Applied Biosystems of Foster City, Calif. The passive dye molecule can be selected so as not to take part in a reaction, for example, a PCR reaction, so that fluorescence from the passive dye is substantially without influence from a target nucleic acid sequence and remains constant during the PCR. Fluorescence detected from the passive dye can be used to normalize the fluorescence from the target sequence binding dye by using a standard concentration of the passive dye in one or more of the reaction regions.

The light source can emit excitation beams that include a secondary excitation frequency that causes the passive dye to fluoresce at a secondary emission frequency. The secondary emission frequency can be directed to a detector to generate corresponding secondary data signals. The processor can receive the secondary data signals and compute secondary data representative of the known standard concentration of the passive dye. These data can be used to normalize the primary data, so that, for example, the concentration of the target nucleic acid sequence is normalized to the standard concentration of the passive dye after correcting the concentration computations of the target sequence in proportion to adjustments made in exposure time, and in conjunction with normalization for drift, accounted for by analyzing the secondary emission frequency. Greater details about the use of passive dyes and mathematical transformations using data collected from passive dyes are set forth in the *ABI Prism 7000 Sequence Detection System User Guide,* pages A-1 through A-10, available from Applied Biosystems, which is incorporated herein in its entirety by reference. The secondary excitation frequency can be identical to the primary excitation frequency, and the passive dye can be selected to fluoresce such that the secondary emission frequency can be substantially at the emission frequency of the primary emission beams. In the example of PCR, the primary data signals can be generated during each extension phase of thermal cycling when the target sequence is recombined and the primary dye emission is maximized. The secondary data signals can be generated during each denature phase of thermal cycling when the target sequence is denatured and correspondingly primary dye emission is minimized. Thus, data signals for the primary phase can be substantially representative of the target sequence concentration, and data signals for the secondary phase can be substantially representative of the standard concentration of passive dye Alternatively or additionally, passive dye data can be taken during the hybridization phase.

Suitable excitation and emission filters for use in an optical instrument can be any conventional optical bandpass filters utilizing, for example, optical interference films, each having a bandpass at a frequency that is optimal for either the excitation wavelength of the fluorescent dye or the emission wavelength of the fluorescent dye. Each filter can have very high attenuation for non-bandpass frequencies to prevent "ghost" images from being reflected and to prevent stray light. For SYBR Green dye, for example, the excitation filter bandpass can center around a 485 nm wavelength, and the emission filter bandpass can center around a 555 nm wavelength. As shown in FIGS. 10-12, transition filters 61, 62 can transition from reflection to transmission at a wavelength between these two, for example, at about a 510 nm wavelength, so that light of frequencies less than the transition wavelength can be reflected and higher wavelength light can pass through the filter, or vice versa. In this manner, according to various embodiments, a transition filter can function as one or more of an excitation filter and an emission filter. The excitation filter and/or the emission filter can be tilted to eliminate ghosts.

Figure 13:
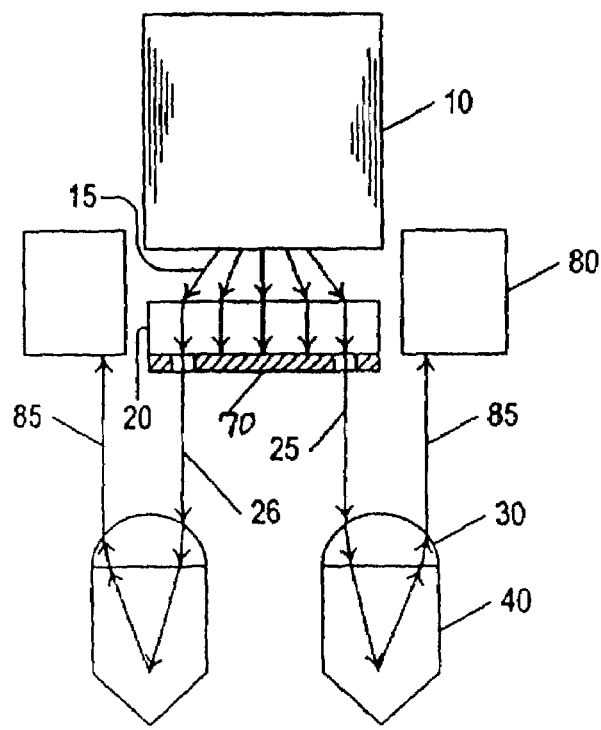
FIG. 13 is a schematic diagram of an optical instrument that includes a light source adjacent a detector, and an optical pathway generated by the optical instrument.
Figure 14:
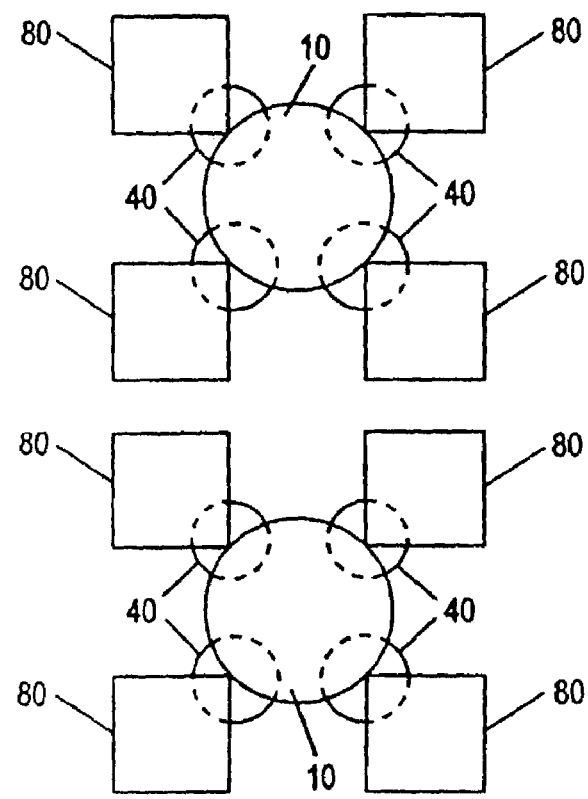
FIG. 14 is a top view of the instrument of FIG. 13.

According to various embodiments, the transition filter can be omitted, and the light source 10 and detector 80 can be located side-by-side as shown in FIGS. 13 and 14, wherein bundles 25 of collimated excitation beams and emission beams 85 pass along slightly different optical paths. Light source 10 and detector 80 need not actually be side-by-side if one or more fold mirrors are used. Thus, any such arrangement for achieving the effects described herein can be used. According to exemplary embodiments, when using a transition filter, bundles of collimated excitation beams 25 and emission beams 85 will have the same optical paths through a focusing lens and/or reaction region lens 30.

Figure 15:
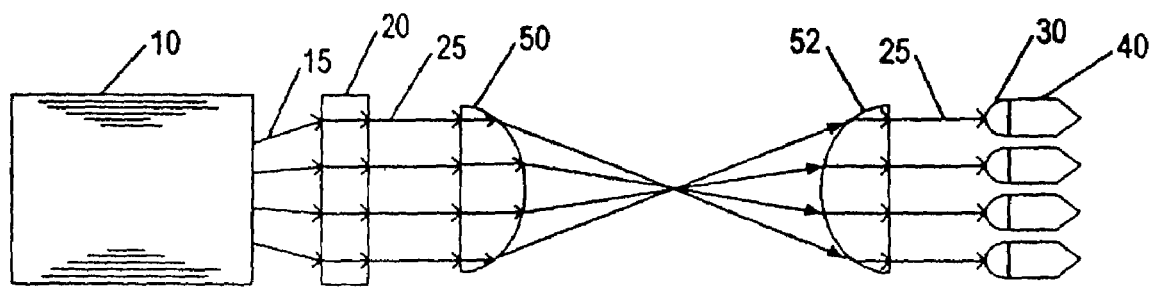
FIG. 15 is a schematic diagram of an optical instrument and an optical pathway according to various embodiments.
Figure 16:
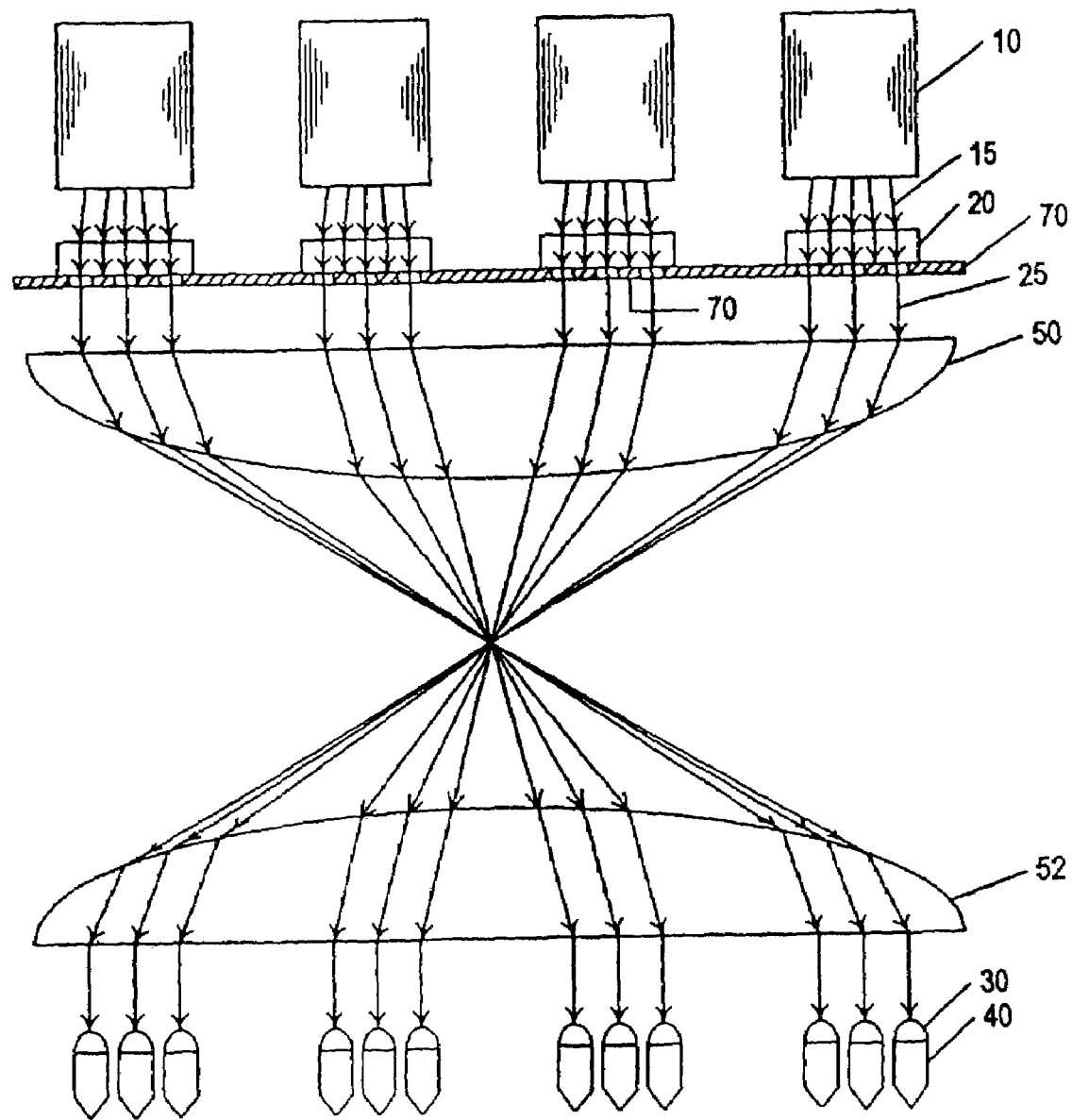
FIG. 16 is a schematic diagram of an optical instrument and an optical pathway, according to various embodiments.

According to various embodiments, as shown in FIGS. 15 and 16, one or more field lens 50, 52 can be used in the optical instrument. The field lens can be a Fresnel lens, or any other suitable lens as known to practitioners in the art. According to various embodiments, first and second field lenses 50, 52 can be positioned such that the first field lens 50 can receive the bundles of collimated excitation beams from the collimating lens and pass the bundles of collimated excitation beams to the second field lens 52, which can be located a distance from the first field lens 50 equal to the sum of the focal lengths of the first and second field lenses 50, 52. The second field lens 52 can collimate the passed excitation beams to create an array of bundles of collimated excitation light parallel to the optical axis of the second field lens 52. The parallel bundles of collimated excitation light can propagate from the second field lens 52 to a reaction region lens or array, or directly to a plurality of spaced-apart reaction regions. According to various embodiments, each bundle of collimated excitation light impinges on a respective reaction region lens or reaction region.

According to various embodiments, for example, as shown in FIG. 15, a pair of field lenses 50, 52 can be used with each light source. According to various other embodiments, as shown, for example, in FIG. 16, a pair of field lenses 50, 52 can be used with multiple light sources. For example, one pair of field lenses can be used for a single line of light sources in a multi-well sample array. In this manner, an 8×12 array of sample wells, totaling 96 sample wells, can have 96 pairs of field lenses (one field lens pair per light source), 12 pairs of field lenses (one field lens pair per row of 8 sample wells), 8 pairs of field lenses (one field lens pair per row of 12 sample wells), or other suitable numbers of field lens pairs. According to various embodiments, a field lens pair can be used in combination with one light source, two light sources, or more than two light sources. The use of one pair of field lenses per multiple light sources can reduce the cost of the optical instrument.

According to various embodiments, a transition filter can be located between a first field lens and a second field lens, such that the bundles of collimated excitation beams can pass through the first field lens and the transition filter to the second field lens. According to various embodiments, the emission beam can pass through the second field lens to the transition filter, which can pass the emission beam to a detector. According to various embodiments, a transition filter can be located between a first field lens and a second field lens such that the bundles of collimated excitation beams pass through the first field lens and are reflected from the transition filter toward the second field lens, and the emission beam passes through the second field lens and the transition filter to a detector. According to various other embodiments, the transition filter can be located between the collimating lens and the first field lens, between the first field lens and the second field lens, or between the second field lens and the reaction region lens or reaction region.

According to various embodiments, methods are provided whereby respective bundles of collimated excitation beams can impinge on respective ones of a plurality of spaced-apart reaction regions. The respective bundles of collimated excitation beams can cause one or more dye in the respective reaction region to fluoresce, emitting an emission beam. According to various embodiments, the emission beam can pass through a reaction region lens and, optionally, a focusing lens or a second field lens, to impinge upon a transition filter. According to various embodiments, the emission beam can pass through the transition filter to detector 80, as shown in FIG. 2. According to various other embodiments, the emission beam is reflected off the transition filter towards detector 80, as shown in FIGS. 10-12. The detector can determine the wavelength of the emission beam as a first data set. The first data set can be sent to processor 90, as shown in FIGS. 2 and 10, for determination of the presence of or absence of fluorescence in a sample in one or more spaced-apart reaction region. The wavelength and strength of the emission beams can also be detected and recorded in the first data set. According to various embodiments, one or more of the reaction region lens, focusing lens, second field lens, or filter can be absent.

According to various embodiments, the detector 80 can be an array detector, for example, a charge injection device (CID), or a charge-coupled device (CCD). A conventional video camera, for example, one containing a CCD detector, can be used. The detector lens 82 and associated electronics for the detector can be those known to those skilled in the art. An exemplary detector system is the Electrim model 1000L, which can include 751 active pixels horizontally and 242 (non-interlaced) active pixels vertically, and can include a circuit board that directly interfaces to a computer ISA bus. Such cameras can include framegrabber circuitry. Any other digital imaging device or subsystem can be used, or adapted and used, such as CMOS pixels, photodiodes, photomultipliers, or other light receptors as known to those of ordinary skill in the art. According to various embodiments, the detector can be capable of taking still or freeze-frame images for post processing in a computer.

According to various embodiments, a detector such as a CCD can receive light for a selected integration period and, after analog/digital conversion, can read out digital signal data at a level accumulated over that period. An electronic shutter can effectively control the integration period. Signal data can be generated for each pixel, including those receiving the emission beam from each of the reaction regions.

A detector including a multiplicity of photoreceptors (pixels) can be used with a plurality of reaction regions in order to provide separate monitoring of each reaction region. According to various embodiments, a scanning device can be used with a single photodetector, for example, by scanning the fold mirror 65 and using a small aperture detector lens 82 for the detector 80, as shown in FIG. 2. According to various embodiments, a plurality of photomultipliers can be used.

According to various embodiments, a detector lens 82 can be used to focus the emission beam onto detector 80. In another embodiment, a focusing reflector can be substituted for detector lens 82. Such an emission focusing system (detector lens or reflector) can be located after (as shown in FIG. 2) or before transition filter 60 on either side of emission filter 120, and alternatively can be integrated into a primary focusing system that includes components also used to direct the excitation beams. For example, a focusing lens 35 can be an objective lens that focuses emission beams 85 onto detector 80.

Detector lens 82 can cooperate with reaction region lens 30 and/or focusing lens 35 to focus the emission beam on detector 80. Detector lens 82 can have a large aperture, a low distortion, and minimum vignetting.

According to various embodiments, a single detector 80 can be used to receive the emission beam from multiple reaction regions 40, as shown in FIGS. 2 and 10, for example. According to various other embodiments, as shown, for example, in FIGS. 13 and 14, each reaction region can correspond to a single detector. Examples of such detectors can be found, for example, in publication WO 01/69211 A1, incorporated herein by reference in its entirety.

According to various embodiments, the processor 90 can be a computer or computer system for determination of the absence or presence and amount of sample components determined by detection of the fluorescence of various fluorescent dyes in the spaced-apart reaction regions. The processor can produce a second data set containing the quantities of various components within each of the plurality of spaced-apart reaction regions.

According to various embodiments, a method of illuminating multiple spaced-apart reaction regions with a light source can comprise emitting light as an excitation beam from a light source, and passing the light through a collimating lens to form bundles of collimated excitation beams wherein each collimated excitation beam lies parallel to the optical axis of the collimating lens after passing through the collimating lens. The bundles of collimated excitation beams can impinge on a plurality of spaced-apart reaction regions such that each bundle of collimated excitation beams is focused on a respective reaction region. To aid in focusing each bundle on a separate reaction region, a reaction region lens, focusing lens, or both can be set in the path of a bundle of collimated excitation beams to focus the bundle on a discrete spaced-apart reaction region. A reaction region lens array can be used to focus the bundles of collimated excitation beams such that each respective bundle of collimated excitation beams is focused into a respective one of a plurality of spaced-apart reaction regions. In various embodiments, a mask or filter block can be disposed after the collimating lens and can be adjacent the collimating lens such that the excitation beams passing through the collimating lens also pass through the mask or filter block to strip unwanted excitation beams from the bundles of collimated excitation beams. The mask or filter block can form a profile of bundles of collimated excitation beams that matches the profile of the plurality of spaced-apart reaction regions set to receive such bundles of collimated excitation beams.

According to various embodiments, the bundles of collimated excitation beams emitted from the collimating lens or mask on the collimating lens can pass through one or more field lenses. The bundles of collimated excitation beams can pass through the first field lens and continue past a focal point of the first field lens until, in various embodiments, they reach a folding mirror or transition filter. The focused bundles of collimated excitation beams can be reflected off the mirror or transition filter, or in the case of the transition filter, can pass through the transition filter, to a second field lens. The second field lens can recollimate the bundles of excitation beams. Each of the recollimated bundles of excitation beams can pass through a respective reaction region lens in order to focus each bundle of excitation beams into a respective reaction region of the plurality of reaction regions. According to various embodiments, the focused bundles of collimated excitation beams, after passing through the first field lens, can continue through the focal point of the first field lens to the second field lens without passing through or impinging on a mirror or transition filter. According to various embodiments, the mask can be located before the reaction region lens to reduce noise.

Once the bundles of collimated excitation beams reach their respective reaction regions, each bundle can impinge upon a respective sample contained or retained in a respective reaction region. Each sample can become excited by the respective bundle of excitation beams and emit emission beams from the sample in the reaction region. The emission beams can pass through the reaction region lens and, according to various embodiments, can impinge on a detector. According to various embodiments, the emission beams can pass through the reaction region lens and then pass through one or more field lens, a transition filter, or any combination thereof before impinging upon a detector. According to various embodiments, the emission beams can pass through a reaction region lens and a transition filter, and into a detector. According to various embodiments, the detector can receive emission beams from a sample in a reaction region and can create a first data set, which can be passed to a processor for determination of the composition of the sample in the reaction region.

Figure 17:
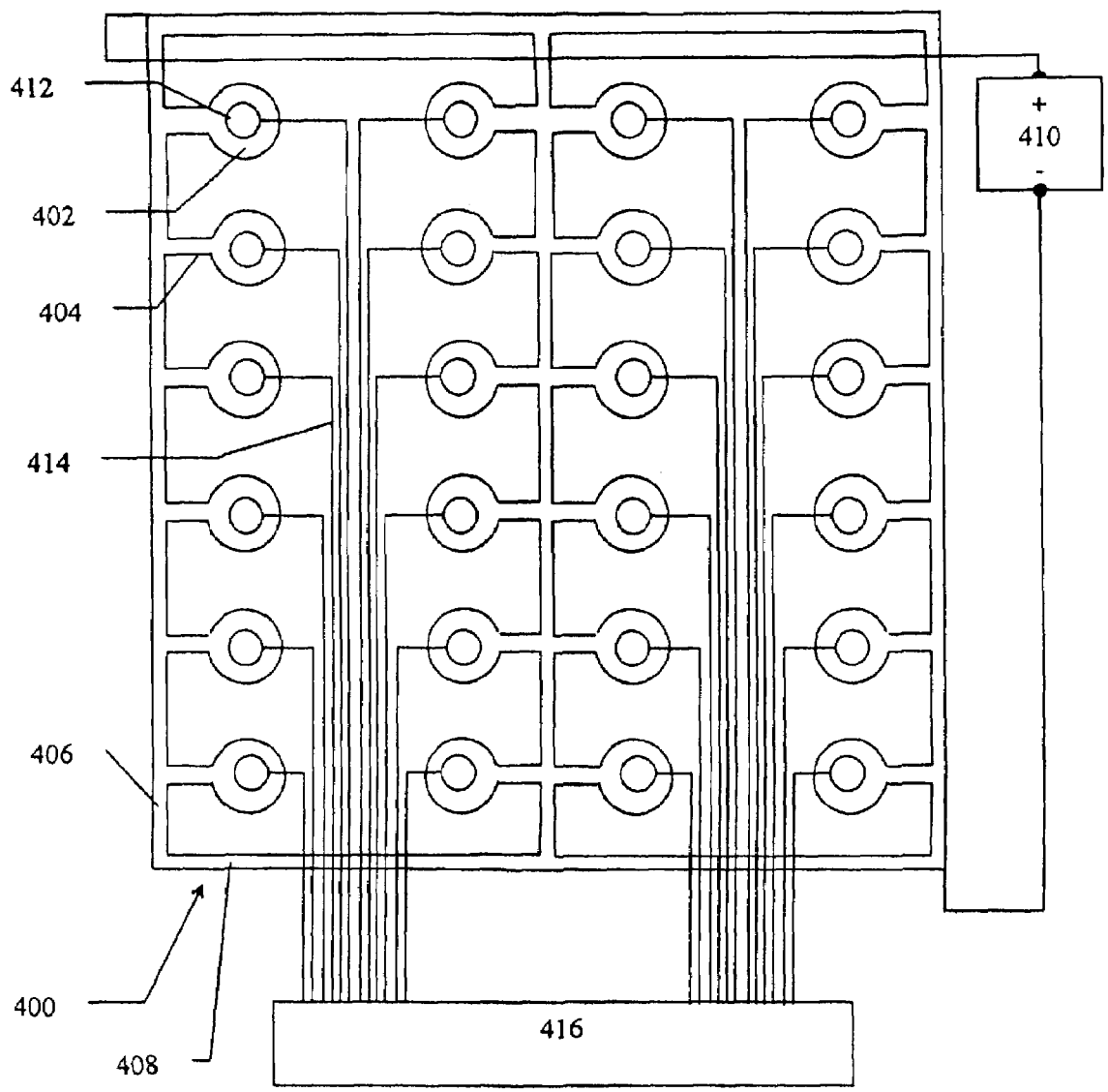
FIG. 17 illustrates an exemplary embodiment of a light source layout, for example, an organic light emitting diode (OLED) layout.

FIG. 17 is a bottom view that illustrates an OLED layout 400 that can be used as a light source, together with a plurality of photodiode detectors 412, according to various embodiments. The OLED layout 400 can include a plurality of OLED well lamps 402, each positioned, when in operation, above a respective well of a multi-well sample well array. Each OLED material well lamp 402 can be connected to, or integrally formed with, a respective connection arm 404 that leads to a layout terminal 406. Each layout terminal can be connected to or integrally formed with the respective connection arms 404 branching from the layout terminal.

The connection arms 404 branch off of side terminals 406 and 408. The OLED layout can be connected to respective opposite electrical connections, for example, opposite terminals of a power supply. The OLED layout can be connected to the power supply through leads arranged at opposite corners of the OLED layout. The power supply can include or be connected to one or more of a switch, a meter, an oscillator, a potentiometer, a detector, a signal processing unit, or the like. Alternatively, or additionally, connection arms 404 can each include a wire or electrical lead in the form of, for example, a metal wire. The OLED layout can include a plurality of individually addressable OLED lighting elements (not shown) with a separate lead connected to each lighting element. The wiring, leads, terminals, connection arms, and the like can be implemented in, for example, a substrate or a film. An OLED layout control unit 410 can be used to supply power and control the OLED layout 400. A plurality of detectors 412 can be electrically connected to a detector control unit 416 through respective detector leads 414 as shown.

The plurality of detectors can be arranged, for example, centered, on the plurality of OLED well lamps 402, on the sides of well lamps that face respective sample wells, and/or when operatively positioned adjacent a multi-well sample well array. The detectors can be configured to detect light emitted from the sample wells of a sample well array, without being flooded or bleached out by the respective OLED well lamps. For example, a mask material can be disposed between the detectors and the respective OLED well lamps. The detector 412 can be formed in the same substrate as the OLED lamp.

The exemplary OLED layout shown in FIG. 17 is shaped to be aligned with a 24 well sample well array. Other embodiments of OLED layouts using various shapes and various numbers of well lamps are within the scope of the present teachings.

According to various embodiments, each well lamp 402 can include, for example, four individual lamps or OLED layers, capable of producing excitation wavelengths at four different frequencies.

The OLED layout can be constructed of a unitary or multi-part construction, of molded material, of stamped material, of screen printed material, of cut material, or the like.

Figure 18:
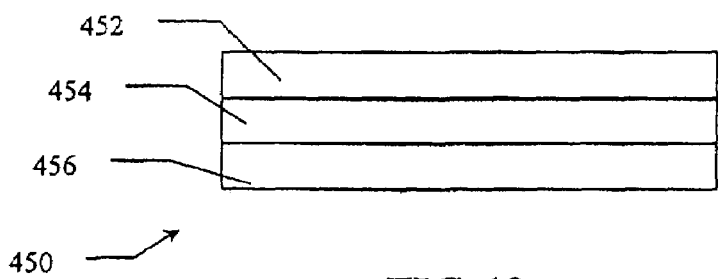
FIG. 18 illustrates an exemplary embodiment of a light source layout, for example, an OLED layout with varying color OLEDs stacked upon each other.

FIG. 18 illustrates an exemplary embodiment of a light source layout. An OLED layout 450 can include varying color OLEDs 452, 454, and 456 stacked upon each other. The layout can be useful for a compact light source design capable of forming excitation beams at varying wavelengths. The OLEDs 452, 454, and 456 can be transparent, allowing excitation beams from each OLED to pass through any other OLED so as to be directed towards a sample. The OLEDs 452, 454, and 456 can emit different colors, same colors, or a combination thereof depending on the color intensity and variety required. The OLEDs 452, 454, and 456 can share an electrode, for example, a cathode. One electrode, for example, an anode, for powering each of the OLEDs 452, 454, and 456 can be connected in electrical isolation from each respective anode to a control unit (not shown) if the capability to independently activate each of the OLEDs 452, 454, and 456 is desired. The OLEDs 452, 454, and 456 can electrically share one electrode, two electrodes, or no electrodes. Any number of OLEDs can be stacked, for example, two OLEDs, three OLEDs, four OLEDs, or more OLEDs, to form a light source, a respective light source, or an array of light sources.

Other embodiments will be apparent to those skilled in the art from consideration of the present specification and practice of the teachings disclosed herein. It is intended that the present specification and examples be considered as exemplary only.

What is claimed is:

1. An instrument comprising:
   a block with a plurality of spaced-apart reaction regions;
   a light emitting diode source adapted to generate a diverging area flood light directing excitation beams toward the plurality of reaction regions;
   a detector disposed to receive emission beams emitted from the plurality of reaction regions; and
   a collimating lens system disposed along a path of the diverging area flood light between the light emitting diode source and the plurality of reaction regions, disposed between the plurality of reaction regions and the detector, and spaced apart from the plurality of reaction regions, wherein the collimating lens system is capable of collimating excitation beams from the diverging area flood light into two or more spaced-apart discrete bundles of collimated excitation beams parallel to an optical axis of the collimating lens system, wherein the discrete bundles are separated from one another and each discrete bundle exits the collimating lens system before irradiating a respective one of the plurality of reaction regions, and each discrete bundle irradiates a respective one of the plurality of spaced-apart reaction regions separate from the reaction regions irradiated by the other discrete bundles of the two or more spaced-apart discrete bundles.

2. The instrument of claim 1, further comprising:
   a focusing lens disposed along a pat of at least one of the two or more bundles of collimated excitation beams between the collimating lens system and the plurality of reaction regions.

3. The instrument of claim 2, wherein the focusing lens is disposed adjacent the reaction region.

4. The instrument of claim 2, wherein the focusing lens is a Fresnel lens.

5. The instrument of claim 1, wherein the collimating lens system includes a collimating lens and a mask.

6. The instrument of claim 1, wherein a sample is disposed in at least one of the reaction regions and the sample includes a dye that is capable of emitting an emission beam when illuminated with a respective one of two or more bundles of collimated excitation beams.

7. The instrument of claim 6, wherein the sample comprises components for nucleic acid sequence amplification.

8. The instrument of claim 7, wherein the sample comprises components for polymerase chain reaction.

9. The instrument of claim 1, wherein the plurality of reaction regions comprises 96 reaction regions.

10. The instrument of claim 1, wherein the collimating lens is disposed about one focal length of the collimating lens away from the light emitting diode source.

11. The instrument of claim 1, wherein the light emitting diode source comprises a light emitting diode having a wattage of greater than about one microwatt.

12. The instrument of claim 1, wherein the light emitting diode has a wattage of about 5 microwatts or greater.

13. The instrument of claim 1, further comprising an excitation filter disposed along an excitation beam path between the light emitting diode source and the plurality of reaction regions.

14. The instrument of claim 13, wherein the excitation filter comprises a long pass filter, a bandpass filter, a multiple bandpass filter, or a combination thereof.

15. The instrument of claim 1, wherein there is a correspondence of 1 to at least 4 between the light emitting diode source and the bundles of collimated excitation beams, respectively.

16. The instrument of claim 1, wherein the collimating lens system comprises a Fresnel lens.

17. The instrument of claim 1, wherein the collimating lens system comprises a molded glass sphere.

18. The instrument of claim 1, further comprising a mask disposed between the collimating lens system and the plurality of reaction regions.

19. The instrument of claim 18, wherein the mask is optically opaque.

20. The instrument of claim 18, wherein the mask comprises anodized aluminum.

21. The instrument of claim 18, wherein the mask is in contact with the collimating lens system.

22. The instrument of claim 20, wherein the mask is adjacent a focusing lens, and the focusing lens is disposed along a beam path of two or more bundles of collimated excitation beams between the collimating lens system and the plurality of reaction regions.

23. The instrument of claim 1, further comprising at least one field lens disposed along an excitation beam path between the collimating lens system and the plurality of reaction regions.

24. The instrument of claim 23, wherein the at least one field lens comprises a Fresnel lens.

25. The instrument of claim 23, comprising two field lenses spaced-apart by the sum of the focal lengths of the two field lenses.

26. The instrument of claim 1, further comprising a mirror disposed along an excitation beam path between the collimating lens system and the plurality of reaction regions.

27. The instrument of claim 1, further comprising a transition filter disposed along an excitation beam path between the collimating lens system and the plurality of reaction regions.

28. The instrument of claim 27, wherein the transition filter comprises a long pass filter, a bandpass filter, a multiple bandpass filter, or a combination thereof.

29. The instrument of claim 1, further comprising a detector disposed to receive emission beams emitted from each of the plurality of reaction regions.

30. The instrument of claim 29, wherein the detector comprises a camera, a charge-coupled detector, a photodiode, a photomultiplier, a CMOS, a CID, or a combination thereof.

31. The instrument of claim 29, wherein the detector is capable of generating a first data set, representative of detected emission beams, and wherein the instrument further comprises a processor capable of receiving a first data set from the detector and processing the first data set.

32. The instrument of claim 1, wherein the light emitting diode source includes an organic light emitting diode.

33. The instrument of claim 1, wherein the block is a thermal cycler block.

34. The instrument of claim 1, wherein the instrument further comprises a thermal cycle controller capable of cycling the temperature of the block.

35. The instrument of claim 1, wherein the two or more bundles of the collimated excitation beams are simultaneously directed toward the respective reaction regions.

36. An instrument comprising:
a block with a plurality of spaced-apart reaction regions;
a solid state laser source adapted to generate a diverging area flood light directing excitation beams toward the plurality of reaction regions;
a detector disposed to receive emission beams emitted from the plurality of reaction regions; and
a collimating lens system disposed along a pat of the diverging area flood light between the solid state laser source and the plurality of reaction regions, and disposed between the plurality of reaction regions and the detector, wherein the collimating lens system is capable of collimating excitation beams from the diverging area flood light into two or more spaced-apart discrete bundles of collimated excitation beams parallel to an optical axis of the collimating lens system, wherein the discrete bundles are separated from one another and each discrete bundle exits the collimating lens system before irradiating a respective one of the plurality of reaction regions, and each discrete bundle irradiates a respective one of the plurality of reaction regions separate from the reaction regions irradiated by the other discrete bundles of the two or more spaced-apart discrete bundles.

37. The instrument of claim 36, further comprising:
a focusing lens disposed along a path of at least one of the two or more bundles of collimated excitation beams between the collimating lens system and the plurality of reaction regions.

38. The instrument of claim 37, wherein the focusing lens is disposed adjacent the reaction region.

39. The instrument of claim 37, wherein the focusing lens is a Fresnel lens.

40. The instrument of claim 36, wherein the block is a thermal cycler block.

41. The instrument of claim 36, wherein the instrument further comprises a thermal cycle controller capable of cycling the temperature of the block.

42. The instrument of claim 36, wherein the two or more bundles of the collimated excitation beams are simultaneously directed toward the respective reaction regions.

43. A method of illuminating a plurality of spaced-apart reaction regions with excitation beams, the method comprising:
providing an instrument comprising a light emitting diode source, a collimating lens system, and a block including the plurality of spaced-apart reaction regions, at least one of the reaction regions comprising a sample;
generating a diverging area flood light with the light emitting diode source;
passing the diverging area flood light through the collimating lens system to form two or more spaced-apart discrete bundles of collimated excitation beams parallel to an optical axis of the collimating lens system, wherein the discrete bundles are separated from one another and each discrete bundle exits the collimating lens system before irradiating a respective one of the plurality of reaction regions;
directing each of the two or more spaced-apart discrete bundles of the collimated excitation beams into a respective one of the regions of the plurality of spaced-apart reaction regions separate from the reaction regions irradiated by the other discrete bundles of the two or more spaced-apart discrete bundles; and
passing emission beams from the spaced-apart reaction regions through the collimating lens system.

44. The method of claim 43, further comprising detecting emission beams emitted from the plurality of spaced-apart reaction regions, with a detector.

45. The method of claim 44, further comprising generating a fast dataset representative of emission beams detected by the detector.

46. The method of claim 43, further comprising processing the first data set with a processor.

47. The method of claim 44, further comprising passing emission beams emitted from the plurality of spaced-apart reaction regions through an emission filter.

48. The method of claim 43, further comprising passing the two or more spaced-apart bundles of collimated excitation beams from the collimating lens system through a first field lens, and from the first field lens through a second field lens.

49. The method of claim 43, wherein the step of directing each of the two or more spaced-apart bundles of collimated excitation beams comprises passing each of the two or more spaced-apart bundles of collimated excitation beams through a focusing lens.

50. The method of claim 49, wherein each focusing lens is a reaction region lens disposed adjacent a respective reaction region.

51. The method of claim 49, wherein the focusing lens is a Fresnel lens.

52. The method of claim 43, further comprising removing extraneous excitation beams with a mask.

53. The method of claim 50, wherein the mask is disposed along an excitation beam path between the collimating lens system and the plurality of reaction regions.

54. The method of claim 43, wherein the sample comprises components for a nucleic acid sequence amplification reaction.

55. The method of claim 54, wherein the nucleic acid sequence amplification reaction comprises a polymerase chain reaction.

56. The method of claim 43, further comprising thermally cycling the sample.

57. The method of claim 56, wherein the instrument further comprises a thermal cycle controller capable of cycling the temperature of the block.

58. The method of claim 43, wherein the block is a thermal cycler block.

59. The method of claim 43, wherein the step of directing the two or more bundles of the collimated excitation beams comprises simultaneously directing the two or more bundles of the collimated excitation beams toward the respective reaction regions.

60. A method of illuminating a plurality of spaced-apart reaction regions with excitation beams, the method comprising:
providing an instrument comprising a solid state laser source, a collimating lens system, and a block including the plurality of spaced-apart reaction regions, at least one of the reaction regions comprising a sample;
generating a diverging area flood light with the solid state laser source;
passing the diverging area flood light through the collimating lens system to form two or more spaced-apart discrete bundles of collimated excitation beams parallel to an optical axis of the collimating lens system, wherein the discrete bundles are separated from one another and each discrete handle exits the collimating lens system before irradiating a respective one of the plurality of reaction regions;
directing each of the two or more spaced-apart discrete bundles of collimated excitation beams into a respective one of the regions of the plurality of spaced-apart reaction regions separate from the reaction regions irradiated by the other discrete bundles of the two or more spaced-apart discrete bundles; and
passing emission beams from the spaced-apart reaction regions through the collimating lens system.

61. The method of claim 60, wherein the step of directing each of the two or more spaced-apart bundles of collimated excitation beams comprises passing each of the two or more spaced-apart bundles of collimated excitation beams through a focusing lens.

62. The method of claim 61, wherein each focusing lens is a reaction region lens disposed adjacent a respective reaction region.

63. The method of claim 61, wherein the focusing lens is a Fresnel lens.

64. The method of claim 60, further comprising thermally cycling the sample.

65. The method of claim 64, wherein the instrument further comprises a thermal cycle controller capable of cycling the temperature of the block.

66. The method of claim 60, wherein the block is a thermal cycler block.

67. The method of claim 60, wherein the step of directing the two or more bundles of the collimated excitation beams comprises simultaneously directing the two or more bundles of the collimated excitation beams toward the respective reaction regions.

68. A method of illuminating a plurality of spaced-apart reaction regions with excitation beams, the method comprising:
providing an instrument comprising a laser source, a collimating lens system, and a block including the plurality of spaced-apart reaction regions, at least one of the reaction regions comprising a sample;
generating excitation beams with the laser source;
passing the excitation beams through the collimating lens system to form two or more spaced-apart discrete bundles of collimated excitation beams parallel to an optical axis of the collimating lens system;
focusing each of the two or more spaced-apart discrete bundles of collimated excitation beams into a the respective ones one of the plurality of spaced-apart reaction regions separate from the reaction regions irradiated by the other discrete bundles of the two or more spaced-apart discrete bundles; and
passing emission beams from the spaced-apart reaction regions through the collimating lens system.

69. The method of claim 68, wherein the step of focusing each of the two or more spaced-apart bundles of collimated excitation beams comprises passing each of the two or more spaced-apart bundles of collimated excitation beams through a focusing lens.

70. The method of claim 69, wherein each focusing lens is a reaction region lens disposed adjacent a respective reaction region.

71. The method of claim 69, wherein the focusing lens is a Fresnel lens.

72. The method of claim 68, further comprising thermally cycling the sample.

73. The method of claim 72, wherein the instrument further comprises a thermal cycle controller capable of cycling the temperature of the block.

74. The method of claim 68, wherein the block is a thermal cycler block.

* * * * *